United States Patent
Bloomfield et al.

(10) Patent No.: US 8,901,134 B2
(45) Date of Patent: *Dec. 2, 2014

(54) PYRAZOLO [3,4-D] PYRIMIDINE DERIVATIVES USEFUL TO TREAT RESPIRATORY DISORDERS

(71) Applicant: Novartis AG, Basel (CH)

(72) Inventors: Graham Charles Bloomfield, Broadbridge Heath (GB); Ian Bruce, Billingshurst (GB); Brian Cox, Horsham (GB); Lee Edwards, Partridge Green (GB); Judy Fox Hayler, East Grinstead (GB); Catherine Howsham, Horsham (GB)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/261,890

(22) Filed: Apr. 25, 2014

(65) Prior Publication Data

US 2014/0235632 A1 Aug. 21, 2014

Related U.S. Application Data

(63) Continuation of application No. 14/049,706, filed on Oct. 9, 2013, which is a continuation of application No. 12/227,314, filed as application No. PCT/EP2007/004501 on May 21, 2007, now abandoned.

(30) Foreign Application Priority Data

May 23, 2006 (GB) .................................. 0610242.0

(51) Int. Cl.
- *A01N 43/90* (2006.01)
- *A61K 31/519* (2006.01)
- *C07D 487/00* (2006.01)
- *C07D 487/04* (2006.01)

(52) U.S. Cl.
CPC ............ *C07D 487/04* (2013.01); *A61K 31/519* (2013.01)
USPC ....................................... 514/262.1; 544/262

(58) Field of Classification Search
CPC .......................... A61K 31/4162; C07D 403/04
USPC ........................................ 514/262.1; 544/262
See application file for complete search history.

(56) References Cited

U.S. PATENT DOCUMENTS

| 4,001,230 A | 1/1977 | Friedman |
| 4,044,130 A | 8/1977 | Howarth et al. |
| 6,518,277 B1 | 2/2003 | Sadhu et al. |

FOREIGN PATENT DOCUMENTS

| WO | WO 01/019829 | 3/2001 |
| WO | WO 03/029209 | 4/2003 |
| WO | WO 03/082341 | 10/2003 |
| WO | WO 03082341 A1 * | 10/2003 |
| WO | WO 2005/007085 | 1/2005 |
| WO | WO 2005/074603 | 8/2005 |
| WO | WO 2006/068760 | 6/2006 |

OTHER PUBLICATIONS

Balram Dhawan et al., "4- Aminopyrazolo[3,4-d]pyrimidines" *Organic Preparations and Procedures Intl* 13(5):379-382, 1981
Zachary A. Knight et al., "A Pharmacological Man of the PI3-K Family Defines a Role of p110 (alpha) in Insulin Signaling" *Cell* 125:733-747, May 2006.
Philip L. Southwick et al., "Preparation of 4,6-Diaminopyrazolo[3-4d]pyrimidines with Variations in Substitution at the 1- and 3- Positions" *J. Heterocyclic Chem.* 12(6):1199-1205, Dec. 1975.
Knox et al., *Thorax*, 2005, BMJ Publishing Group 60:88-89.
Vippagunta et al., Advanced Drug Delivery Reviews, 2001 Elsevier 48:3-26.

* cited by examiner

*Primary Examiner* — Sarah Pihonak
(74) *Attorney, Agent, or Firm* — Michael G. Smith

(57) ABSTRACT

The present invention concerns a compound of formula (I)

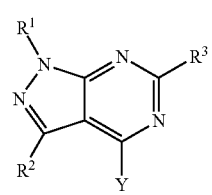

or a pharmaceutically acceptable salt or solvate thereof, where $R^1$-$R^3$ and Y are defined in the description, and its use in the treatment of disorders in which pi3 kinase is implicated.

13 Claims, No Drawings

PYRAZOLO [3,4-D] PYRIMIDINE DERIVATIVES USEFUL TO TREAT RESPIRATORY DISORDERS

CROSS-REFERENCE TO RELATED APPLICATIONS

This application is a continuation application of U.S. Ser. No. 14/049,706, filed Oct. 9, 2013, which is a continuation application of U.S. Ser. No. 12/227,314, filed Nov. 12, 2008, now abandoned, which was the National Phase filing of International Application Serial No. PCT/EP2007/004501 filed May 21, 2007 and claims priority to United Kingdom Application No. 0610242.0, filed May 23, 2006, the contents of which are incorporated herein by reference in their entirety.

FIELD OF THE INVENTION

The present invention relates to organic compounds, their preparation and their use as pharmaceuticals.

International Patent Application Publication No. WO03029209 describes pyrazolo[3,4-d]pyrimidines useful as pharmaceuticals.

In a first aspect, the present invention provides use of a compound of formula (I)

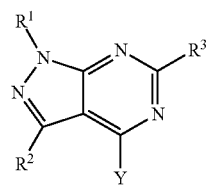

(I)

or a salt, suitably a pharmaceutically acceptable salt, or solvate thereof, wherein:

$R^1$ is $C_1$-$C_3$-alkyl, optionally substituted by one to seven fluoro groups;

$R^2$ is a 5-6 membered hetaroaryl group, or $R^2$ is phenyl having the substitution pattern,

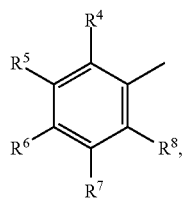

where the 5-6 membered heteroaryl group is optionally fused by phenyl, a further 5-6 membered heteroaryl group, a $C_4$-$C_6$ carbocyclic group or a 5-6 membered heterocyclyl group and where the $R^2$ phenyl is optionally fused at $R^4$-$R^5$, $R^5$-$R^6$, $R^6$-$R^7$ or $R^7$-$R^8$ by a further phenyl, a 5-6 membered heteroaryl group, a $C_4$-$C_6$ carbocyclic group or a 5-6 membered heterocyclyl group, where the 5-6 membered heteroaryl or fused 5-6 membered heteroaryl, phenyl or the fused phenyl group is independently optionally substituted by one or more groups selected from List X;

List X represents hydroxyl, cyano, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, phenyl, a 5-6 membered heteroaryl group, a $C_4$-$C_6$ carbocyclic group or a 5-6 membered heterocyclyl group, —($C_0$-$C_4$-alkylene)-O—($C_1$-$C_4$-alkylene)-$R^9$, ($C_0$-$C_4$-alkylene)-O—($C_2$-$C_4$-alkylene)-$R^{10}$, ($C_0$-$C_4$-alkylene)-N($R^{11}$)—($C_1$-$C_4$-alkylene)-$R^{12}$, —($C_0$-$C_4$-alkylene)-N($R^{13}$)—($C_2$-$C_4$-alkylene)-$R^{14}$, halogen, formyl, $C_1$-$C_8$-alkylcarbonyl, carboxy, $C_1$-$C_8$-alkoxycarbonyl, $C_1$-$C_8$-alkylaminooxycarbonyl, di-$C_1$-$C_8$-alkylaminooxycarbonyl, amino, $C_1$-$C_8$-alkylamino, di-$C_1$-$C_8$-alkylamino, $C_1$-$C_8$-alkylamidino, —N(H)C(=NH)$C_1$-$C_8$-alkyl, —N($C_1$-$C_8$-alkyl)C(=NH)$C_1$-$C_8$-alkyl, $C_1$-$C_8$-alkylaminocarbonyl, di-$C_1$-$C_8$-alkylaminocarbonyl, aminocarbonylamino, aminocarbonyl($C_1$-$C_8$-alkyl)amino, $C_1$-$C_8$-alkylaminocarbonylamino, di-$C_1$-$C_8$-alkylaminocarbonylamino, $C_1$-$C_8$-alkylaminocarbonyl($C_1$-$C_8$-alkyl)amino, di-$C_1$-$C_8$-alkylaminocarbonyl($C_1$-$C_8$-alkyl)amino, $C_1$-$C_8$-alkylcarbonylamino, $C_1$-$C_8$-alkylcarbonyl($C_1$-$C_8$-alkyl)amino, $C_1$-$C_8$-alkylthiocarbonylamino, $C_1$-$C_8$-alkylthiocarbonyl($C_1$-$C_8$-alkyl)amino, hydroxysulfonyl, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl, where each of the afore-mentioned hydrocarbon groups may be optionally substituted, where chemically feasible, by one or more halogen, hydroxyl, amino, $C_1$-$C_4$-alkylamino, di-$C_1$-$C_4$-alkylamino or $C_1$-$C_4$-alkoxy groups and where said cyclic groups may be optionally substituted by one or more hydroxyl, cyano, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups;

$R^9$ and $R^{12}$ independently represent hydrogen, $C_1$-$C_4$-alkenyl, $C_1$-$C_4$-alkynyl, halogen, cyano, nitro, $C_1$-$C_8$-alkylcarbonyl, carboxy, $C_1$-$C_8$-alkoxycarbonyl, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl, di-$C_1$-$C_8$-alkylaminosulfonyl, phenyl, a C-linked 5-6 membered heteroaryl group, a $C_4$-$C_6$ carbocyclic group or a C-linked 5-6 membered heterocyclyl group, where said phenyl or cyclic groups may be optionally substituted by one or more hydroxyl, cyano, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups;

$R^{10}$ and $R^{14}$ independently represent hydroxyl, $C_1$-$C_4$-alkoxy, $C_1$-$C_4$-alkenyloxy, $C_1$-$C_4$-alkynyloxy, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, an N-linked 5-6 membered heteroaryl group or an N-linked 5-6 membered heterocycly where said cyclic groups may be optionally substituted by one or more hydroxyl, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups;

$R^{11}$ and $R^{13}$ independently represent hydrogen or $C_1$-$C_6$-alkyl;

$R^3$ is hydrogen, amino or $C_1$-$C_3$-alkylamino;

Y represents hydrogen, $C_1$-$C_8$-alkyl, $C_1$-$C_8$-alkoxy where each of the afore-mentioned hydrocarbon groups may be optionally substituted, where chemically feasible, by one or more halogen, hydroxyl, amino, $C_1$-$C_8$-alkylamino, di-$C_1$-$C_8$-alkylamino or $C_1$-$C_8$-alkoxy groups, or Y represents the group —($C_0$-$C_4$-alkylene)-N($R^{15}$)$R^{16}$; and $R^{15}$ and $R^{16}$ independently represent hydrogen or $C_1$-$C_4$-alkyl, or $R^{15}$ is hydrogen and $R^{16}$ is $C_1$-$C_4$-alkyl substituted by phenyl, a 5-6 membered heteroaryl group, a $C_4$-$C_6$ carbocyclic group or a 5-6 membered heterocyclyl group, where said rings are optionally substituted by one or more hydroxyl, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups, where each of the afore-mentioned hydrocarbon groups may be optionally substituted, where chemically feasible by one or more halogen, hydroxyl, amino, $C_1$-$C_4$-alkylamino, di-$C_1$-$C_4$-alkylamino or $C_1$-$C_4$-alkoxy groups, or $R^{15}$ and $R^{16}$ together with the N to which they are attached form a 5-6-membered heterocyclic ring; in the treatment of, or in the manufacture of a medicament for the treatment of, a disorder in which pi3 kinase, particularly pi3 kinase gamma, is implicated, particularly a respiratory disorder, such as asthma or COPD.

As a yet further alternative aspect, there is provided a method of treating a disorder in which pi3 kinase is implicated in a patient comprising administering an effective amount of a compound of formula (I), or a pharmaceutically acceptable salt or solvate thereof. Suitably, the disorder is selected from a respiratory disorder, such as asthma or COPD.

In a further aspect of the present invention, there is provided a compound of formula (I), or a pharmaceutically acceptable salt or solvate thereof, with the proviso that the compounds N-[4-[6-(ethylamino)-1-methyl-1H-pyrazolo[3,4-d]pyrimidin-3-yl]phenyl]-N'-[2-fluoro-5-(trifluoromethyl)phenyl urea and [4-(6-amino-1-methyl-1H-pyrazolo[3,4-d]pyrimidin-3-yl)phenyl]-1,1-dimethyl carbamic acid ester are excluded.

In a yet further aspect, the present invention provides a compound of formula (IA):

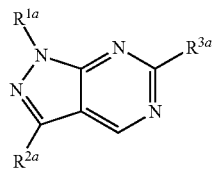

(IA)

or a salt, suitably a pharmaceutically acceptable salt, or solvate thereof, wherein:

$R^{1a}$ is $C_1$-$C_3$-alkyl, optionally substituted by one to seven fluoro groups;

$R^{2a}$ a 5-6 membered hetaroaryl group substituted by one or more groups selected from List Xa, or $R^2$ is phenyl having the substitution pattern,

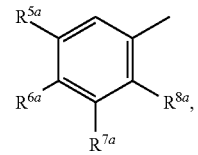

where the phenyl may be fused at $R^{5a}$-$R^{6a}$, $R^{6a}$-$R^{7a}$ or $R^{7a}$-$R^{8a}$ by a 5-6 membered heteroaryl group, a $C_4$-$C_6$ carbocyclic group or a 5-6 membered heterocyclyl group, where the phenyl or the fused phenyl group may be optionally substituted by one or more groups selected from List Xa;

List Xa represents hydroxyl, cyano, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, —O—($C_1$-$C_4$-alkylene)-$R^{9a}$, —O—($C_2$-$C_4$-alkylene)-$R^{10a}$, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl, where each of the afore-mentioned hydrocarbon groups may be optionally substituted by one or more halogen, hydroxyl or $C_1$-$C_8$-alkoxy groups;

$R^{9a}$ represents $C_1$-$C_4$-alkenyl, $C_1$-$C_4$-alkynyl, halogen, cyano, nitro, $C_1$-$C_8$-alkylcarbonyl, carboxy, $C_1$-$C_8$-alkoxycarbonyl, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl, di-$C_1$-$C_8$-alkylaminosulfonyl, phenyl, a C-linked 5-6 membered heteroaryl group, a $C_4$-$C_6$ carbocyclic group or a C-linked 5-6 membered heterocyclyl group, where said phenyl or cyclic groups may be optionally substituted by one or more hydroxyl, cyano, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups;

$R^{10a}$ represents hydroxyl, $C_1$-$C_4$-alkoxy, $C_1$-$C_4$-alkenyloxy, $C_1$-$C_4$-alkynyloxy, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, an N-linked 5-6 membered heteroaryl group or an N-linked 5-6 membered heterocycly where said cyclic groups may be optionally substituted by one or more hydroxyl, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$- alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups; and $R^{3a}$ is hydrogen, amino or $C_1$-$C_3$-alkylamino.

Alkyl, alkenyl, alkynyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

A "hydrocarbon group optionally substituted" refers to replacement of a C—H bond by the requisite bond. Where the substituent is a halogen, the group formed is defined as a $C_1$-$C_8$-haloalkyl. For example, where the substituent is fluoro, common haloalkyl groups are trifluoroalkyl, 2,2,2-trifluoroethyl or 2,2,2,1,1-pentafluoroethyl groups.

"Carbocyclic group" denotes a hydrocarbon ring having the requisite number of carbon atoms, for example cyclopropyl, cyclobutyl, cyclopentyl, cyclohexyl, cycloheptyl or cyclooctyl.

"Halogen" or "halo" may be fluorine, chlorine, bromine or iodine.

A heterocyclyl group refers to a saturated or partially unsaturated ring comprising one or more O, N or S heteratoms. Specific examples of heterocyclyl groups include [1,3]dioxolane, [1,4]dioxane, oxiranyl, aziridinyl, oxetanyl, azetidinyl, tetrahydrofuranyl, pyrrolidinyl, tetrahydropyranyl, piperidinyl, morpholino, thiomorpholinyl, piperazinyl, azepinyl, oxapinyl, oxazepinyl and diazepinyl.

A heteroaryl group refers to an aromatic ring comprising one or more O, N or S heteroatoms. Examples of heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl, and bicyclic heteroaryl or phenyl fused by heteroaryl groups include indolyl, quinolinyl, isoquinolinyl, benzimidazolyl and benzofuranyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The following suitable or preferred features of a compound of formula (I) may be incorporated into the definition of formula (I) and combined individually or in any combination. It will be understood that the compounds of formula (IA) are equivalent to the compounds of formula (I) though the R groups do not correspond, and that the suitable and preferred features of compounds of formula (I) apply equally to compounds of formula (IA).

According to formula (I), $R^1$ is suitably methyl or trifluoromethyl, preferably methyl.

According to formula (I), the $R^2$ ring is suitably substituted.

According to formula (I), where $R^2$ is an optionally substituted heteroaryl, including fused heteroaryl, the heteroaryl is suitably
  (i) pyridyl, e.g. 3-pyridyl or 4-pyridyl, optionally substituted by halogen, e.g. fluoro, trifluoromethyl, methylsulfonyl or $C_1$-$C_8$-alkoxy, e.g. methoxy,
  (ii) thienyl, e.g. 2-thienyl, optionally substituted by $C_1$-$C_8$-alkylcarbonyl, e.g. acetyl, or halo, e.g. chloro,
  (iii) isoxazolyl, e.g. 4-isoxazolyl, optionally substituted by one or two $C_1$-$C_8$-alkyl, e.g. 3,5-dimethyl,
  (iv) furanyl, e.g. 2-furanyl, or
  (v) pyrimidyl, e.g. 5-pyrimidyl, optionally substituted by a 5-6 membered heterocyclyl, e.g. piperazinyl, e.g. 2-piperazinyl or one or two $C_1$-$C_8$-alkoxy, e.g. 2-methoxy or 2,4 dimethoxy.

Where the $R^2$ phenyl ring is fused by a further phenyl to form a naphthyl group, the ring is suitably fused at $R^7$-$R^8$ to form a 1-naphthyl, and the resulting naphthyl is optionally substituted, e.g. by $C_1$-$C_8$-alkoxy, e.g. ethoxy, e.g. 2-ethoxy.

Where the $R^2$ phenyl ring is fused by a 5-6 membered heteroaryl, the ring is suitably fused at $R^5$-$R^6$, $R^6$-$R^7$, or $R^7$-$R^8$, suitably by a pyridine, pyrrole or furan ring. Where an indole or benzofuran ring is formed, this is suitably 5- or 6-linked. Where a quinolinyl ring is formed, this is suitably 8-linked. Said rings are optionally substituted, e.g. an indole ring may be suitably optionally substituted, e.g. by one or more $C_1$-$C_8$-alkyl, e.g. 2,3-dimethyl.

Where the $R^2$ phenyl ring is fused by a 5-6 membered heterocyclyl, the ring is suitably fused at $R^5$-$R^6$, e.g. to form a benzo 1,3-dioxole or a 2,3-Dihydro-benzo[1,4]dioxine group.

Where $R^2$ is a substituted phenyl, suitable substituents from List X are one two, three or four substituents, suitably two or three substituents selected from
  (i) hydroxyl,
  (ii) cyano,
  (iii) nitro,
  (iv) $C_1$-$C_8$-alkyl, e.g. methyl or isobutyl,
  (v) $C_1$-$C_8$-haloalkyl, e.g. trifluoromethyl,
  (vi) $C_1$-$C_8$-alkoxy, e.g. methoxy, ethoxy, n-propoxy, isopropoxy,
  (vii) a 5-6 membered heterocyclyl group, e.g. N-piperazinyl,
  (viii) —O—($C_1$-$C_4$ alkylene)-$R^9$, e.g. O-methylene-$R^9$, e.g. carboxymethoxy, cyanomethoxy or optionally substituted benzyloxy, e.g. benzyloxy or 2-fluorobenzyloxy,
  (ix) —O—($C_2$-$C_4$ alkylene)-$R^{10}$, e.g. O-ethylene or propylene-$R^{10}$, e.g. N-pyrrolidylethoxy, N-imidazolylethoxy, N-morpholinoethoxy, methoxyethoxy, hydroxyethoxy, hydroxypropoxy or N-morpholinopropoxy,
  (x) —($C_0$-$C_4$-alkylene)-$N(R^{13})$—($C_2$-$C_4$-alkylene)-$R^{14}$, where $C_0$-$C_4$ alkylene is suitably methylene, $R^{13}$ is suitably hydrogen, $C_2$-$C_4$ alkylene is suitably n-propylene and $R^{14}$ is suitably di-$C_1$-$C_8$-alkylamino, e.g. dimethylamino, e.g. to form dimethylaminopropylaminomethyl,
  (xi) halogen, e.g. fluoro, chloro or bromo,
  (xii) formyl,
  (xiii) $C_1$-$C_8$-alkylcarbonyl, e.g. acetyl,
  (xiv) $C_1$-$C_8$-alkylaminocarbonyl, e.g. methylaminocarbonyl, isopropylaminocarbonyl or isobutylaminocarbonyl,
  (xv) di-$C_1$-$C_8$-alkylaminocarbonyl, e.g. dimethylaminocarbonyl,
  (xvi) $C_1$-$C_8$-alkylcarbonylamino, e.g. methylcarbonylamino,
  (xvii) $C_1$-$C_8$-alkylsulfonylamino, e.g. methylsulfonylamino,
  (xviii) hydroxysulfonyl,
  (xix) $C_1$-$C_8$-alkylsulfonyl, e.g. methylsulfonyl,
  (xx) $C_1$-$C_8$-alkylaminosulfonyl, e.g. methylaminosulfonyl or isopropylaminosulfonyl,
  (xxi) di-$C_1$-$C_8$-alkylaminosulfonyl, e.g. dimethylaminosulfonyl,
  (xxii) $C_1$-$C_8$-alkyl substituted by hydroxy, e.g. hydroxymethyl, (xxiii) $C_1$-$C_8$-alkoxy substituted by one or more, e.g. three halogens, e.g. fluoro, e.g. trifluoromethoxy, and (xxiv) amino.

According to formula (I), $R^9$ suitably represents carboxy, cyano or phenyl, optionally substituted, e.g. by halogen, e.g. fluoro, e.g. 2-fluoro.

According to formula (I), $R^{10}$ suitably represents hydroxyl, $C_1$-$C_4$-alkoxy, an N-linked 5-6 membered heteroaryl group, e.g. N-imidazolyl or an N-linked 5-6 membered heterocycly, e.g. N-pyrrolidyl or N-morpholino.

According to formula (I), $R^{13}$ is suitably hydrogen.

According to formula (I), $R^{14}$ is suitably di-$C_1$-$C_8$-alkylamino, e.g. dimethylamino.

Where $R^2$ is a substituted phenyl, $R^4$-$R^8$ may be substituted by any combination of selections of the following suitable substituents, suitably one, two, three or four of $R^4$-$R^8$, more suitably two or three.

$R^4$ is suitably selected from hydrogen, $C_1$-$C_8$-alkoxy, e.g. methoxy or n-propoxy and halogen, e.g. fluoro.

$R^5$ is suitably selected from hydrogen, hydroxyl, cyano, formyl, $C_1$-$C_8$-haloalkyl, e.g. trifluoromethyl, carboxy, $C_1$-$C_8$-alkoxy, e.g. methoxy, halogen, e.g. fluoro, chloro or bromo, $C_1$-$C_8$-alkylcarbonyl, e.g. acetyl, $C_1$-$C_8$-alkylaminocarbonyl, e.g. methylaminocarbonyl, isopropylaminocarbonyl or isobutylcarbonyl, di-$C_1$-$C_8$-alkylaminocarbonyl, e.g. dimethylaminocarbonyl, $C_1$-$C_8$-alkylsulfonylamino, e.g. methylsulfonylamino, $C_1$-$C_8$-thioalkyl, $C_1$-$C_8$-alkylsulfinyl, $C_1$-$C_8$-alkylsulfonyl, e.g. methylsulfonyl, —($C_0$-$C_4$ alkylene)-N($R^{13}$)—($C_2$-$C_4$ alkylene)-$R^{14}$, e.g. dimethylaminopropylaminomethyl, $C_1$-$C_8$-alkyl substituted by hydroxy, e.g. hydroxymethyl, and hydroxysulfonyl.

$R^6$ is suitably selected from hydrogen, hydroxyl, cyano, nitro, formyl, carboxy, $C_1$-$C_8$-alkyl, e.g. methyl or isobutyl, $C_1$-$C_8$-alkoxy e.g. methoxy, ethoxy or isopropoxy, —O—($C_1$-$C_4$ alkylene)-$R^9$, suitably O-methylene-$R^9$, e.g. benzyloxy or cyanomethoxy, —O—($C_2$-$C_4$ alkylene)-$R^{10}$, suitably O-ethylene or propylene-$R^{10}$, e.g. N-pyrrolidylethoxy, imidazolylethoxy, N-morpholinoethoxy, methoxyethoxy, hydroxyethoxy, hydroxypropoxy or N-morpholinopropoxy, halogen, e.g. fluoro or chloro, $C_1$-$C_8$-alkylcarbonyl, e.g. acetyl, amino, $C_1$-$C_8$-alkylaminocarbonyl, e.g. isopropylaminocarbonyl, $C_1$-$C_8$-alkylsulfonylamino, e.g. methylsulfonylamino, $C_1$-$C_8$-alkylsulfonyl, e.g. methylsulfonyl, and $C_1$-$C_8$-alkoxy substituted by one or more, e.g. three halogens, e.g. fluoro, e.g. trifluoromethoxy.

$R^7$ is suitably selected from hydrogen, hydroxyl, formyl, $C_1$-$C_8$-alkoxy, e.g. methoxy, halogen, e.g. bromo, chloro or fluoro, —O—($C_1$-$C_4$ alkylene)-$R^9$, e.g. carboxymethoxy, $C_1$-$C_8$-alkylcarbonylamino, e.g. methylcarbonylamino, and di-$C_1$-$C_8$-alkylaminosulfonyl, e.g. dimethylaminosulfonyl.

$R^8$ is suitably selected from hydrogen, hydroxyl, $C_1$-$C_8$-alkoxy, e.g. methoxy, —O—($C_2$-$C_4$ alkylene)-$R^{10}$, e.g. O-ethylene-O—$R^{10}$, e.g. hydroxyethoxy, and —O—($C_1$-$C_4$ alkylene)-$R^9$, suitably O-methylene—$R^9$, e.g. benzyloxy.

Preferably, $R^4$ is selected from hydrogen, methoxy, n-propoxy and fluoro.

Preferably, $R^5$ is selected from hydrogen, hydroxyl, cyano, formyl, trifluoromethyl, carboxy, methoxy, fluoro, chloro, bromo, acetyl, methylaminocarbonyl, isopropylaminocarbonyl, isobutylcarbonyl, dimethylaminocarbonyl, methylsulfonylamino, methylsulfonyl, dimethylaminopropylaminomethyl hydroxymethyl and hydroxysulfonyl.

Preferably, $R^6$ selected from hydrogen, hydroxyl, cyano, nitro, formyl, carboxy, methyl, isobutyl, methoxy, ethoxy, isopropoxy, benzyloxy, cyanomethoxy, N-pyrrolidylethoxy, imidazolylethoxy, N-morpholinoethoxy, methoxyethoxy, hydroxyethoxy, hydroxypropoxy, N-morpholinopropoxy, fluoro, chloro, acetyl, amino, isopropylaminocarbonyl, methylsulfonylamino, methylsulfonyl and trifluoromethoxy, Preferably, $R^7$ is selected from hydrogen, hydroxyl, formyl, methoxy, bromo, chloro, fluoro, carboxymethoxy, methylcarbonylamino and dimethylaminosulfonyl.

Preferably, $R^8$ is selected from hydrogen, hydroxyl, methoxy, hydroxyethoxy and benzyloxy.

When $R^2$ is phenyl, a preferred substitution pattern is where $R^2$ is substituted by at least a fluoro group at $R^5$.

Most preferably, $R^2$ is
3-fluoro-4-methoxy-phenyl,
3-fluoro-4-hydroxy-phenyl,
3-fluoro-4-(methylsulfonylamino)-phenyl,
3-fluoro-4-hydroxy-5-bromo-phenyl,
3,5-bromo-4-hydroxy-phenyl,
3-fluoro-4-(hydroxyethoxy)phenyl, or
3-fluoro-4-hydroxy-5-methoxy-phenyl.

According to formula (I), $R^3$ is suitably hydrogen, amino or methylamino, preferably amino.

According to formula (I), Y is suitably Y hydrogen, or Y represents the group $N(R^{15})R^{16}$, where $R^{15}$ is suitably hydrogen and $R^{16}$ is suitably $C_1$-$C_4$-alkyl, e.g. methyl or ethyl, substituted by an optionally substituted phenyl or 5-6 membered heterocyclyl group, e.g. N-morpholino, N-piperidyl, N-piperazinyl, where optional substituents are one, two or three of hydroxyl, cyano, nitro, $C_1$-$C_8$-alkyl, $C_1$-$C_8$-alkoxy, halogen, formyl, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl.

More suitably, Y is hydrogen, benzylamino or morpholin-4-yl-ethylamino, most suitably hydrogen.

A sub-formula of the present invention is represented by a compound of formula (IB)

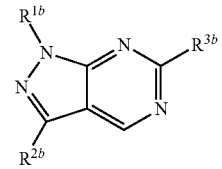

(IB)

or a salt, suitably a pharmaceutically acceptable salt, or solvate thereof, wherein:

$R^{1b}$ is methyl;

$R^{2b}$ is phenyl substituted by one two, three or four substituents, suitably two or three substituents selected from hydroxyl, cyano, nitro, halogen, formyl, amino. $C_1$-$C_8$-alkyl, $C_8$-haloalkyl, $C_1$-$C_8$-alkoxy, a 5-6 membered heterocyclyl group, —O—($C_1$-$C_4$ alkylene)-$R^{9b}$, —O—($C_2$-$C_4$ alkylene)-$R^{19b}$, —($C_0$-$C_4$ alkylene)-N(H)—($C_2$-$C_4$ alkylene)-$R^{14b}$, $C_1$-$C_8$-alkylcarbonyl, $C_1$-$C_8$-alkylaminocarbonyl, di-$C_1$-$C_8$-alkylaminocarbonyl, dimethylaminocarbonyl, $C_1$-$C_8$-alkylcarbonylamino, $C_1$-$C_8$-alkylsulfonylamino, hydroxysulfonyl, $C_1$-$C_8$-alkylsulfonyl, $C_1$-$C_8$-alkylaminosulfonyl, di-$C_1$-$C_8$-alkylaminosulfonyl, $C_1$-$C_8$-alkyl substituted by hydroxy, $C_1$-$C_8$-alkoxy substituted by one or more fluoro; where each of the afore-mentioned hydrocarbon groups may be optionally substituted, where chemically feasible, by one to five halogen or by hydroxyl, amino, $C_1$-$C_4$-alkylamino, di-$C_1$-$C_4$-alkylamino or $C_1$-$C_4$alkoxy;

$R^{3b}$ is amino;

$R^{9b}$ represents carboxy, cyano or phenyl, optionally substituted by one, two or three halogen;

$R^{10b}$ represents hydroxyl, $C_1$-$C_4$alkoxy, an N-linked 5-6 membered heteroaryl group or an N-linked 5-6 membered heterocyclyl; and $R^{14b}$ is di-$C_1$-$C_8$-alkylamino.

A suitable individual compound of the invention is selected from:

3-(3-Fluoro-4-methoxy-phenyl)-1-methyl-1H-pyrazolo[3,4-d]pyrimidin 6-ylamine;
3-(4-Ethoxy-3-fluoro-phenyl)-1-methyl-1H-pyrazolo[3,4-d]pyrimidin-6 ylamine;
3-(3-Fluoro-4-isopropoxy-phenyl)-1-methyl-1H-pyrazolo[3,4d]pyrimidin-6-ylamine;
3-(4-Methoxy-phenyl)-1-methyl-1H-pyrazolo[3,4-d]pyrimidin-6-ylamine;
3-(3-Chloro-4-methoxy-phenyl)-1-methyl-1H-pyrazolo[3,4-d]pyrimidin 6-ylamine;
3-(3-Bromo-4-methoxy-phenyl)-1-methyl-1H-pyrazolo[3,4-d]pyrimidin 6-ylamine;
3-(3-Chloro-4-isopropoxy-phenyl)-1-methyl-1H-pyrazolo[3,4d]pyrimidin-6-ylamine;
3-Benzo[1,3]dioxol-5-yl-1-methyl-1H-pyrazolo[3,4-d]pyrimidin-6 ylamine;
3-(2,3-Dihydro-benzo[1,4]dioxin-6-yl)-1-methyl-1H-pyrazolo[3,4d]pyrimidin-6-ylamine;
1-Methyl-3-(3,4,5-trimethoxy-phenyl)-1H-pyrazolo[3,4-d]pyrimidin-6-ylamine;
3-(3-Fluoro-phenyl)-1-methyl-1H-pyrazolo[3,4-d]pyrimidin-6-ylamine;
3-(3,4-Difluoro-phenyl)-1-methyl-1H-pyrazolo[3,4-d]pyrimidin-6-ylamine;
3-(3-Chloro-4-fluoro-phenyl)-1-methyl-1H-pyrazolo[3,4-d]pyrimidin-6-ylamine;
3-(3,4-Dichloro-phenyl)-1-methyl-1H-pyrazolo[3,4-d]pyrimidin-6-ylamine;
3-(3-Bromo-5-fluoro-phenyl)-1-methyl-1H-pyrazolo[3,4-d]pyrimidin-6-ylamine;
3-(5-Fluoro-2-methoxy-phenyl)-1-methyl-1H-pyrazolo[3,4-d]pyrimidin-6-ylamine;
3-(3,5-Difluoro-2-methoxy-phenyl)-1-methyl-1H-pyrazolo[3,4-d]pyrimidin-6-ylamine;
3-(2,3-Dimethyl-1H-indol-5-yl)-1-methyl-1H-pyrazolo[3,4-d]pyrimidin-6-ylamine;
3-(7-Fluoro-1H-indol-5-yl)-1-methyl-1H-pyrazolo[3,4-d]pyrimidin-6-ylamine;
3-Benzofuran-6-yl-1-methyl-1H-pyrazolo[3,4-d]pyrimidin-6-ylamine;
1-Methyl-3-(3-trifluoromethyl-phenyl)-1H-pyrazolo[3,4-d]pyrimidin-6-ylamine;
1-[3-(6-Amino-1-methyl-1H-pyrazolo[3,4-d]pyrimidin-3-yl)-phenyl]-ethanone;
3-(6-Amino-1-methyl-1H-pyrazolo[3,4-d]pyrimidin-3-yl)-benzonitrile;
3-(3-Methanesulfonyl-phenyl)-1-methyl-1H-pyrazolo[3,4-d]pyrimidin-6-ylamine;
N-[3-(6-Amino-1-methyl-1H-pyrazolo[3,4-d]pyrimidin-3-yl)-phenyl]-methanesulfonamide;
1-[4-(6-Amino-1-methyl-1H-pyrazolo[3,4-d]pyrimidin-3-yl)-phenyl]-ethanone;
4-(6-Amino-1-methyl-1H-pyrazolo[3,4-d]pyrimidin-3-yl)-benzonitrile;
1-Methyl-3-pyridin-4-yl-1H-pyrazolo[3,4-d]pyrimidin-6-ylamine;
3-(2-Chloro-pyridin-4-yl)-1-methyl-1H-pyrazolo[3,4-d]pyrimidin-6-ylamine;
3-(2-Methoxy-pyridin-4-yl)-1-methyl-1H-pyrazolo[3,4-d]pyrimidin-6-ylamine;
1-Methyl-3-pyridin-3-yl-1H-pyrazolo[3,4-d]pyrimidin-6-ylamine;
3-(6-Methoxy-pyridin-3-yl)-1-methyl-1H-pyrazolo[3,4-d]pyrimidin-6-ylamine;
3-(5-Fluoro-6-methoxy-pyridin-3-yl)-1-methyl-1H-pyrazolo[3,4-d]pyrimidin-6-ylamine;
1-[5-(6-Amino-1-methyl-1H-pyrazolo[3,4-d]pyrimidin-3-yl)-thiophen-2-yl]-ethanone;
3-(4-Benzyloxy-3-fluoro-phenyl)-1-methyl-1H-pyrazolo[3,4-d]pyrimidin-6-ylamine;
4-(6-Amino-1-methyl-1H-pyrazolo[3,4-d]pyrimidin-3-yl)-2-fluoro-phenol;
2-(6-Amino-1-methyl-1H-pyrazolo[3,4-d]pyrimidin-3-yl)-4-fluoro-phenol;
3-(6-Amino-1-methyl-1H-pyrazolo[3,4-d]pyrimidin-3-yl)-5-fluoro-phenol;
4-(6-Amino-1-methyl-1H-pyrazolo[3,4-d]pyrimidin-3-yl)-phenol;
3-(6-Amino-1-methyl-1H-pyrazolo[3,4-d]pyrimidin-3-yl)-phenol;
4-(6-Amino-1-methyl-1H-pyrazolo[3,4-d]pyrimidin-3-yl)-2-chloro-6-methoxy-phenol;
4-(6-Amino-1-methyl-1H-pyrazolo[3,4-d]pyrimidin-3-yl)-2-bromo-6-fluoro-phenol;
4-(6-Amino-1-methyl-1H-pyrazolo[3,4-d]pyrimidin-3-yl)-2,6-dibromo-phenol;
3-[3-Bromo-5-fluoro-4-(2-pyrrolidin-1-yl-ethoxy)-phenyl]-1-methyl-1H-pyrazolo[3,4-d]pyrimidin-6-ylamine;
3-[3-Bromo-5-fluoro-4-(2-methoxy-ethoxy)-phenyl]-1-methyl-1H-pyrazolo[3,4-d]pyrimidin-6-ylamine;
2-[4-(6-Amino-1-methyl-1H-pyrazolo[3,4-d]pyrimidin-3-yl)-2-bromo-6-fluoro-phenoxy]-ethanol;
3-[3-Bromo-5-fluoro-4-(2-morpholin-4-yl-ethoxy)-phenyl]-1-methyl-1H-pyrazolo[3,4-d]pyrimidin-6-ylamine;
2-[4-(6-Amino-1-methyl-1H-pyrazolo[3,4-d]pyrimidin-3-yl)-2-fluoro-phenoxy]-ethanol;
3-[4-(6-Amino-1-methyl-1H-pyrazolo[3,4-d]pyrimidin-3-yl)-2-fluoro-phenoxy]-propan-1-ol;
3-[3-Fluoro-4-(2-methoxy-ethoxy)phenyl]-1-methyl-1H-pyrazolo[3,4-d]pyrimidin-6-ylamine;
[4-(6-Amino-1-methyl-1H-pyrazolo[3,4-d]pyrimidin-3-yl)-2-fluoro-phenoxy]-acetonitrile;
3-[3-Fluoro-4-(2-pyrrolidin-1-yl-ethoxy)phenyl]-1-methyl-1H-pyrazolo[3,4-d]pyrimidin-6-ylamine;
3-[3-Fluoro-4-(2-imidazol-1-yl-ethoxy)-phenyl]-1-methyl-1H-pyrazolo[3,4-d]pyrimidin-6-ylamine;
3-[3-Fluoro-4-(2-morpholin-4-yl-ethoxy)phenyl]-1-methyl-1H-pyrazolo[3,4-d]pyrimidin-6-ylamine;
3-[3-Fluoro-4-(3-morpholin-4-yl-propoxy)-phenyl]-1-methyl-1H-pyrazolo[3,4-d]pyrimidin-6-ylamine;
3-{3-Fluoro-4-[3-(4-methyl-piperazin-1-yl)-propoxy]-phenyl}-1-methyl-1H-pyrazolo[3,4-d]pyrimidin-6-ylamine;
2-[2-(6-Amino-1-methyl-1H-pyrazolo[3,4-d]pyrimidin-3-yl)-4-fluoro-phenoxy]-ethanol;
3-(4-Amino-3-fluoro-phenyl)-1-methyl-1H-pyrazolo[3,4-d]pyrimidin-6-ylamine;
N-[4-(6-Amino-1-methyl-1H-pyrazolo[3,4-d]pyrimidin-3-yl)-2-fluoro-phenyl]-methanesulfonamide;
[3-(3-Fluoro-phenyl)-1-methyl-1H-pyrazolo[3,4-d]pyrimidin-6-yl]-methyl-amine, 3-(3,5-Difluoro-phenyl)-1-methyl-1H-pyrazolo[3,4-d]pyrimidin-6-ylamine;
1-Methyl-3-(2,3,4-trifluoro-phenyl)-1H-pyrazolo[3,4-d]pyrimidin-6-ylamine trifluoroacetate;
3-(5-Chloro-thiophen-2-yl)-1-methyl-1H-pyrazolo[3,4-d]pyrimidin-6-ylamine trifluoroacetate;
3-(5-Bromo-2-methoxy-phenyl)-1-methyl-1H-pyrazolo[3,4-d]pyrimidin-6-ylamine trifluoroacetate;
3-(2-Ethoxy-naphthalen-1-yl)-1-methyl-1H-pyrazolo[3,4-d]pyrimidin-6-ylamine trifluoroacetate;
3-[3-Bromo-2-(2-fluoro-benzyloxy)-phenyl]-1-methyl-1H-pyrazolo[3,4-d]pyrimidin-6-ylamine trifluoroacetate;
1-[3-(6-Amino-1-methyl-1H-pyrazolo[3,4-d]pyrimidin-3-yl)-2-fluoro-phenyl]-ethanone;
3-(4-Fluoro-2-propoxy-phenyl)-1-methyl-1H-pyrazolo[3,4-d]pyrimidin-6-ylamine;
3-(3,5-Dimethyl-isoxazol-4-yl)-1-methyl-1H-pyrazolo[3,4-d]pyrimidin-6-ylamine;
1-Methyl-3-m-tolyl-1H-pyrazolo[3,4-d]pyrimidin-6-ylamine;
3-Furan-2-yl-1-methyl-1H-pyrazolo[3,4-d]pyrimidin-6-ylamine;
3-(5-Chloro-2-methoxy-phenyl)-1-methyl-1H-pyrazolo[3,4-d]pyrimidin-6-ylamine;
3-(2,5-Dimethoxy-phenyl)-1-methyl-1H-pyrazolo[3,4-d]pyrimidin-6-ylamine;
1-Methyl-3-(4-methyl-3-nitro-phenyl)-1H-pyrazolo[3,4-d]pyrimidin-6-ylamine;
3-(4-Isobutyl-phenyl)-1-methyl-1H-pyrazolo[3,4-d]pyrimidin-6-ylamine;
3-(6-Amino-1-methyl-1H-pyrazolo[3,4-d]pyrimidin-3-yl)-4-methoxy-benzaldehyde;
1-Methyl-3-(3,4,5-trifluoro-phenyl)-1H-pyrazolo[3,4-d]pyrimidin-6-ylamine; 1-Methyl-3-quinolin-8-yl-1H-pyrazolo[3,4-d]pyrimidin-6-ylamine;
3-(6-Amino-1-methyl-1H-pyrazolo[3,4-d]pyrimidin-3-yl)-N-isopropyl-benzamide;
4-(6-Amino-1-methyl-1H-pyrazolo[3,4-d]pyrimidin-3-yl)-2,6-difluoro-benzaldehyde;
[3-(6-Amino-1-methyl-1H-pyrazolo[3,4-d]pyrimidin-3-yl)-5-fluoro-phenoxy]-acetic acid;
3-(6-Amino-1-methyl-1H-pyrazolo[3,4-d]pyrimidin-3-yl)-N-methyl-benzamide;
1-Methyl-3-(2-piperazin-1-yl-pyrimidin-5-yl)-1H-pyrazolo[3,4-d]pyrimidin-6-ylamine;
3-(2,4-Dimethoxy-pyrimidin-5-yl)-1-methyl-1H-pyrazolo[3,4-d]pyrimidin-6-ylamine;
3-(6-Amino-1-methyl-1H-pyrazolo[3,4-d]pyrimidin-3-yl)-benzaldehyde;
3-(2-Methoxy-pyrimidin-5-yl)-1-methyl-1H-pyrazolo[3,4-d]pyrimidin-6-ylamine;
3-(6-Amino-1-methyl-1H-pyrazolo[3,4-d]pyrimidin-3-yl)-N-isobutyl-benzamide;
3-(6-Amino-1-methyl-1H-pyrazolo[3,4-d]pyrimidin-3-yl)-N-methyl-benzenesulfonamide;
3-(2-Methoxy-5-trifluoromethyl-phenyl)-1-methyl-1H-pyrazolo[3,4-d]pyrimidin-6-ylamine;
3-(2,4-Dimethoxy-phenyl)-1-methyl-1H-pyrazolo[3,4-d]pyrimidin-6-ylamine;
3-(2,6-Dimethoxy-phenyl)-1-methyl-1H-pyrazolo[3,4-d]pyrimidin-6-ylamine;
2-(6-Amino-1-methyl-1H-pyrazolo[3,4-d]pyrimidin-3-yl)-4-trifluoromethyl-phenol;
4-(6-Amino-1-methyl-1H-pyrazolo[3,4-d]pyrimidin-3-yl)-benzene-1,3-diol;
2-(6-Amino-1-methyl-1H-pyrazolo[3,4-d]pyrimidin-3-yl)-4-chloro-phenol;
3-(6-Amino-1-methyl-1H-pyrazolo[3,4-d]pyrimidin-3-yl)-4-methoxy-benzoic acid;
4-(6-Amino-1-methyl-1H-pyrazolo[3,4-d]pyrimidin-3-yl)-2,6-dichloro-phenol;
4-(6-Amino-1-methyl-1H-pyrazolo[3,4-d]pyrimidin-3-yl)-2-chloro-6-fluoro-phenol;
2-(6-Amino-1-methyl-1H-pyrazolo[3,4-d]pyrimidin-3-yl)-6-bromo-4-chloro-phenol;
3-(3,5-Difluoro-4-methoxy-phenyl)-1-methyl-1H-pyrazolo[3,4-d]pyrimidin-6-ylamine;
3-(6-Amino-1-methyl-1H-pyrazolo[3,4-d]pyrimidin-3-yl)-N-isopropyl-4-methoxy-benzamide;
3-(6-Amino-1-methyl-1H-pyrazolo[3,4-d]pyrimidin-3-yl)-4-hydroxy-benzaldehyde;
3-(6-Amino-5-trifluoromethyl-pyridin-3-yl)-1-methyl-1H-pyrazolo[3,4-d]pyrimidin-6-ylamine;
4-(6-Amino-1-methyl-1H-pyrazolo[3,4-d]pyrimidin-3-yl)-2,6-difluoro-benzonitrile;
N-[3-(6-Amino-1-methyl-1H-pyrazolo[3,4-d]pyrimidin-3-yl)-4-methoxy-phenyl]-N',N'-dimethyl-propane-1,3-diamine;
[3-(6-Amino-1-methyl-1H-pyrazolo[3,4-d]pyrimidin-3-yl)-4-methoxy-phenyl]-methanol;
N-[5-(6-Amino-1-methyl-1H-pyrazolo[3,4-d]pyrimidin-3-yl)-3-fluoro-2-methoxy-phenyl]-acetamide;
4-(6-Amino-1-methyl-1H-pyrazolo[3,4-d]pyrimidin-3-yl)-2,6-difluoro-benzoic acid;
5-(6-Amino-1-methyl-1H-pyrazolo[3,4-d]pyrimidin-3-yl)-3-fluoro-2-hydroxy-benzaldehyde;
4-(6-Amino-1-methyl-1H-pyrazolo[3,4-d]pyrimidin-3-yl)-2,6-difluoro-phenol;
5-(6-Amino-1-methyl-1H-pyrazolo[3,4-d]pyrimidin-3-yl)-3-fluoro-2-hydroxy-benzonitrile;
3-(4-Fluoro-2-methoxy-phenyl)-1-methyl-1H-pyrazolo[3,4-d]pyrimidin-6-ylamine;
4-(6-Amino-1-methyl-1H-pyrazolo[3,4-d]pyrimidin-3-yl)-2-trifluoromethyl-phenol;
2-(6-Amino-1-methyl-1H-pyrazolo[3,4-d]pyrimidin-3-yl)-6-fluoro-phenol;
5-(6-Amino-1-methyl-1H-pyrazolo[3,4-d]pyrimidin-3-yl)-2,4-dimethoxy-benzenesulfonic acid;
3-(5-Chloro-2,4-dimethoxy-phenyl)-1-methyl-1H-pyrazolo[3,4-d]pyrimidin-6-ylamine;
4-(6-Amino-1-methyl-1H-pyrazolo[3,4-d]pyrimidin-3-yl)-2-chloro-6-trifluoromethyl-phenol;
5-(6-Amino-1-methyl-1H-pyrazolo[3,4-d]pyrimidin-3-yl)-2-benzyloxy-3-fluoro-N,N-dimethyl-benzamide;
4-(6-Amino-1-methyl-1H-pyrazolo[3,4-d]pyrimidin-3-yl)-6-chloro-benzene-1,3-diol;
3-(3-Chloro-2-methoxy-5-trifluoromethyl-phenyl)-1-methyl-1H-pyrazolo[3,4-d]pyrimidin-6-ylamine;
4-(6-Amino-1-methyl-1H-pyrazolo[3,4-d]pyrimidin-3-yl)-2-bromo-6-chloro-benzene-1,3-diol;
5-(6-Amino-1-methyl-1H-pyrazolo[3,4-d]pyrimidin-3-yl)-2,4-dimethoxy-N-methyl-benzenesulfonamide;
5-(6-Amino-1-methyl-1H-pyrazolo[3,4-d]pyrimidin-3-yl)-N-isopropyl-2,4-dimethoxy-benzenesulfonamide;
2-(6-Amino-1-methyl-1H-pyrazolo[3,4-d]pyrimidin-3-yl)-6-chloro-4-trifluoromethyl-phenol;
3-(2-Methoxy-4-trifluoromethoxy-phenyl)-1-methyl-1H-pyrazolo[3,4-d]pyrimidin-6-ylamine;
2-(6-Amino-1-methyl-1H-pyrazolo[3,4-d]pyrimidin-3-yl)-5-trifluoromethoxy-phenol;
3-(5-Chloro-2-methoxy-4-trifluoromethoxy-phenyl)-1-methyl-1H-pyrazolo[3,4-d]pyrimidin-6-ylamine;
6-(6-Amino-1-methyl-1H-pyrazolo[3,4-d]pyrimidin-3-yl)-2-bromo-4-chloro-3-trifluoromethoxy-phenol;

5-(6-Amino-1-methyl-1H-pyrazolo[3,4-d]pyrimidin-3-yl)-N,N-diethyl-2-hydroxy-benzenesulfonamide;

N-[5-(6-Amino-1-methyl-1H-pyrazolo[3,4-d]pyrimidin-3-yl)-2-chloro-phenyl]-methanesulfonamide;

5-(6-Amino-1-methyl-1H-pyrazolo[3,4-d]pyrimidin-3-yl)-2-chloro-N-methyl-benzenesulfonamide;

3-(5-Methanesulfonyl-pyridin-3-yl)-1-methyl-1H-pyrazolo[3,4-d]pyrimidin-6-ylamine;

3-(1H-Indol-6-yl)-1-methyl-1H-pyrazolo[3,4-d]pyrimidin-6-ylamine;

1-Methyl-3-(5-trifluoromethyl-pyridin-3-yl)-1H-pyrazolo[3,4-d]pyrimidin-6-ylamine hydrochloride;

N*4*-Benzyl-3-(3-fluoro-4-methoxy-phenyl)-1-methyl-1H-pyrazolo[3,4-d]pyrimidine-4,6-diamine;

4-[6-Amino-1-methyl-4-(2-morpholin-4-yl-ethylamino)-1H-pyrazolo[3,4-d]pyrimidin-3-yl]-2,6-dichloro-phenol;

or a salt, suitably a pharmaceutically acceptable salt, or solvate thereof.

Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

In those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof.

Specific preferred compounds of formula I are described hereinafter in the Examples.

The invention provides, in another aspect, a process (A) for preparing a compound of formula I, where $R^1$, $R^2$ and Y are as hereinbefore described and $R^3$ is $NH_2$ or $C_1$-$C_3$-alkylamino, by reaction of a compound of formula (II)

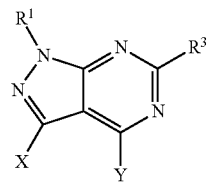

(II)

where Y, $R^1$ and $R^3$ are as hereinbefore described and X represents a suitable boronic acid coupling group, e.g. bromo or chloro, with a compound of $R^2$—$(BOH)_2$ under suitable boronic acid coupling conditions, such as Pd(0)tetrakis triphenylphosphine in 1,4-dioxane-water in the presence of a base such as sodium carbonate. The reaction may be carried out using conventional or microwave radiation heating.

Compounds of formula (II) and $R^2$—$(BOH)_2$ are known or can be prepared by methods well-known to those skilled in the art.

For example, compounds of formula (II) where X is Br, Y is hydrogen, $R^1$=Me and $R^3$ is amino or $C_1$-$C_3$-alkylamino, may be obtained from reacting known compound of formula (III)

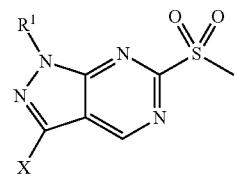

III where X is Br and $R^1$ is Me, with ammonia or $C_1$-$C_3$alkylamino in an organic solvent such as tetrahydrofuran (THF) or 1,4-dioxane, as described in WO2005074603 and WO 2003029209.

Alternatively, compounds of formula (I), where $R^3$ is amino or $C_1$-$C_3$-alkylamino, can be prepared by reaction of a compound of formula (IV) where Y, $R^1$ and $R^2$ are as hereinbefore described, with ammonia or $C_1$-$C_3$-alkylamino in an organic solvent.

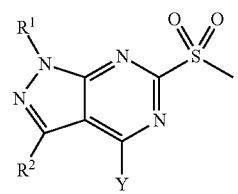

IV

Compounds of formula (IV) may be prepared from compounds of formula (V), where Y, $R^1$ and $R^2$ are as hereinbefore described, by oxidation of the sulphide group using standard procedures for oxidising sulfides to sulfones.

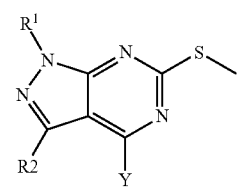

V

Compounds of formula V may be prepared from compounds of formula (VI), where Y and $R^1$ are hereinbefore described and X represents a suitable boronic acid coupling group, e.g. triflate or the known bromo analogue, according to WO2003029209.

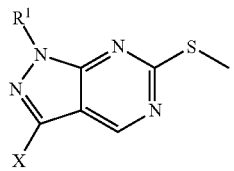

(VI)

Compounds of formula VI where $R^1$ is Me and X is triflate may be prepared from the known compound of formula VI where X is OH according to M. Hauser, E. Peters, H. Tieckelmann, J. Org. Chem., (1960), 25, p1570-1573 and WO2003029209. Compounds of formula (II) where Y is $N(R^{16})NR^{17}$, may be prepared by reaction of a compound of formula (VII)

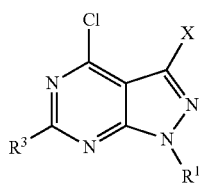

(VII)

with a compound of $HN(R^{16})NR^{17}$ at elevated temperature in a suitable solvent.

A compound of formula (VII) may be prepared by reaction of a compound of formula (VIII)

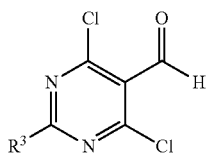

(VIII)

with hydrazine and a suitable base, e.g. triethylamine, in a suitable solvent, such as tetrahydrofuran, followed by bromination or chlorination of the resulting compound using standard methods, e.g. n-chloro or bromo succinimide in dichloroethane, followed by optional alkylation where $R^1$ is not hydrogen. Compounds of formula (VIII) are commercially available or may be readily synthesised by methods well-known in the art.

Compounds of formula I and their pharmaceutically acceptable salts are useful as pharmaceuticals. In particular, they exhibit inhibition of phosphatidylinositol 3-kinase (PI 3-kinase) enzymes, especially the gamma isoform (p110γ), which are responsible for generating phosphorylated signalling products. The inhibitory properties of compounds of formula I may be demonstrated in the following test procedures:

Baculovirus expressing different fragments of human PI 3-Kγ fused to glutathione S-transferase (GST) have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. Biochem. J., 324:489. Residues 38-1102 of human PI 3-Kγ are subcloned into the BamH1 and EcoR1 sites of the transfer vector pAcG2T (Pharmingen) to create a GST-PI 3-Kγ lacking the first 37 residues of PI 3-Kγ. To express the recombinant protein, Sf9 (*Spodoptera frugiperda* 9) insect cells are routinely maintained at densities between $3 \times 10^5$ and $3 \times 10^6$ cells/ml in serum containing TNMFH medium (Sigma). Sf9 cells, at a density of $2 \times 10^6$ are infected with human GST-PI 3-KγΔ34 baculovirus at a multiplicity of infection (m.o.i.) of 1 for 72 hours. The infected cells are harvested by centrifugation at 1400 g for 4 minutes at 4° C. and the cell pellets are frozen at −80° C. Both Sf9 and Sf21 cells work equally well. Sf9 cells ($1 \times 10^9$) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FALCON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1000 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at −20° C.

An in vitro kinase assay was established that measures the transfer of the terminal phosphate of adenosine triphosphate to phosphatidylinositol. The kinase reaction is performed in a white 96 well microtitre plate as a Scintillation Proximity Assay. Each well contains 10 μl test compound in 5% dimethylsulphoxide and 20 μl assay mix (40 mM Tris, 200 mM NaCl, 2 mM ethyleneglycol-aminoethyl-tetraacetic acid (EGTA), 15 μg/ml phosphatidylinositol, 12.5 μM adenosine triphosphate (ATP), 25 mM $MgCl_2$, 0.1 μCi [$^{33}P$]ATP). The reaction is started by the addition of 20 μl of enzyme mix (40 mM Tris, 200 mM NaCl, 2 mM EGTA containing recombinant GST-p110γ). The plate is incubated at room temperature for 60 minutes and the reaction terminated by the adding 150 μl of WGA-bead stop solution (40 mM Tris, 200 mM NaCl, 2 mM EGTA, 1.3 mM ethylene diamine tetraacetic acid (EDTA), 2.6 μM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 μl of 5% dimethylsulphoxide (DMSO) and non-specific activity is determined by adding 10 μl 50 mM EDTA in place of the test compound.

Compounds of the Examples hereinbelow have $IC_{50}$ values below 2 M in the aforementioned assay.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the PI 3-kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include thrombosis, hypertension, heart ischaemia and pancreatitis, (Nature review November 2006 Vol 5), treatment of anaemia including haemolytic anaemia, aplastic anaemia and pure red cell anaemia (WO 2006/040318), septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8. The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone dipropionate, fluticasone propionate, ciclesonide or mometasone furoate and compounds described in WO 0200679, WO 0288167, WO 0212266 and WO 02100879, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)-propyl]-sulfonyl]ethyl]-amino]ethyl]-2(3H)-benzothiazolone and pharmaceutically acceptable salts thereof (the hydrochloride being Viozan®-AstraZeneca), and PDE4 inhibitors such as Ariflo® (GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene) and KW-4490 (Kyowa Hakko Kogyo) as well as those described in WO 98/18796 and WO 03/39544. Such bronchodilatory drugs include anticholinergic or antimuscarinic agents, in particular ipratropium bromide, oxitropium bromide and tiotropium salts but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357 and WO 03/33495, and beta-2 adrenoceptor agonists such as salbutamol, terbutaline, salmeterol and, especially, formoterol and pharmaceutically acceptable salts thereof, and compounds (in free or salt or solvate form) of formula I of PCT International patent publication No. WO 00/75114, which document is incorporated herein by reference, preferably compounds of the Examples thereof, especially 5-[(R)-2-(5,6-Diethyl-indan-2-ylamino)-1-hydroxy-ethyl]-8-hydroxy-1H-quinolin-2-one, and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO00/66558 (particularly claim 8), and WO00/66559 (particularly claim 9).

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefore. The composition may contain a co-therapeutic agent such as an anti-inflammatory, bronchodilatory or antihistamine drug as hereinbefore described. Such compositions may be prepared using conventional diluents or excipients and techniques known in the galenic art. Thus oral dosage forms may include tablets and capsules.

Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

Dosages of agents of the invention employed in practising the present invention will of course vary depending, for example, on the particular condition to be treated, the effect desired and the mode of administration. In general, suitable daily dosages for oral administration are of the order of 0.1 to 10 mg/kg.

EXAMPLES

Preparation of Final Compounds

Compounds of formula I which are also of formula VII

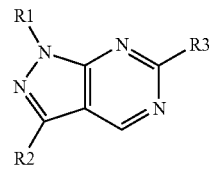

VII are shown in Table 1 below, the method of preparation being described hereinafter. The table also shows mass spectrometry data.

TABLE 1

| Ex. | R¹ | R² | R³ | M/s [M + H]⁺ |
|---|---|---|---|---|
| 1 | CH₃ | 3-fluoro-4-methoxyphenyl | NH₂ | 274 |
| 2 | CH₃ | 3-fluoro-4-ethoxyphenyl | NH₂ | 288 |
| 3 | CH₃ | 3-fluoro-4-isopropoxyphenyl | NH₂ | 302 |
| 4 | CH₃ | 4-methoxyphenyl | NH₂ | 256 |
| 5 | CH₃ | 3-chloro-4-methoxyphenyl | NH₂ | — |
| 6 | CH₃ | 3-bromo-4-methoxyphenyl | NH₂ | 336 |
| 7 | CH₃ | 3-chloro-4-isopropoxyphenyl | NH₂ | 318 |
| 8 | CH₃ | 1,3-benzodioxol-5-yl | NH₂ | 270 |
| 9 | CH₃ | 2,3-dihydro-1,4-benzodioxin-6-yl | NH₂ | 284 |
| 10 | CH₃ | 3,4,5-trimethoxyphenyl | NH₂ | 316 |
| 11 | CH₃ | 3-fluorophenyl | NH₂ | 243 |
| 12 | CH₃ | 3,4-difluorophenyl | NH₂ | 261 |
| 13 | CH₃ | 3-chloro-4-fluorophenyl | NH₂ | 277 |
| 14 | CH₃ | 3,4-dichlorophenyl | NH₂ | 294 |
| 15 | CH₃ | 3-bromo-5-fluorophenyl | NH₂ | 322 |
| 16 | CH₃ | 4-fluoro-2-methoxyphenyl | NH₂ | |
| 17 | CH₃ | 3,5-difluoro-4-methoxyphenyl | NH₂ | 292 |
| 18 | CH₃ | 2,3-dimethyl-1H-indol-5-yl | NH₂ | 293 |
| 19 | CH₃ | 7-fluoro-1H-indol-5-yl | NH₂ | 283 |
| 20 | CH₃ | 1-benzofuran-6-yl | NH₂ | 265 |
| 21 | CH₃ | 3-(trifluoromethyl)phenyl | NH₂ | 294 |

TABLE 1-continued

| Ex. | R¹ | R² | R³ | M/s [M + H]⁺ |
|---|---|---|---|---|
| 22 | CH₃ | 3-acetylphenyl | NH₂ | 268 |
| 23 | CH₃ | 3-cyanophenyl | NH₂ | 251 |
| 24 | CH₃ | 3-(methylsulfonyl)phenyl | NH₂ | 304 |
| 25 | CH₃ | 3-(methylsulfonamido)phenyl | NH₂ | 318 |
| 26 | CH₃ | 4-acetylphenyl | NH₂ | 268 |
| 27 | CH₃ | 4-cyanophenyl | NH₂ | 251 |
| 28 | CH₃ | pyridin-4-yl | NH₂ | 226 |
| 29 | CH₃ | 2-chloropyridin-4-yl | NH₂ | 260 |
| 30 | CH₃ | 2-methoxypyridin-4-yl | NH₂ | 256 |
| 31 | CH₃ | pyridin-3-yl | NH₂ | 226 |
| 32 | CH₃ | 6-methoxypyridin-3-yl | NH₂ | 257 |
| 33 | CH₃ | 5-fluoro-6-methoxypyridin-3-yl | NH₂ | 275 |
| 34 | CH₃ | 5-methyl-2-acetylthiophen-2-yl | NH₂ | 274 |
| 35 | CH₃ | 4-(benzyloxy)-3-fluorophenyl | NH₂ | 350 |
| 36 | CH₃ | 3-fluoro-4-hydroxyphenyl | NH₂ | 259 |
| 37 | CH₃ | 4-fluoro-2-hydroxyphenyl | NH₂ | 260 |
| 38 | CH₃ | 3-fluoro-5-hydroxyphenyl | NH₂ | 260 |
| 39 | CH₃ | 4-hydroxyphenyl | NH₂ | 242 |
| 40 | CH₃ | 3-hydroxyphenyl | NH₂ | 242 |
| 41 | CH₃ | 3-chloro-2-hydroxy-5-methoxyphenyl | NH₂ | 306 |
| 42 | CH₃ | 3-bromo-5-fluoro-2-hydroxyphenyl | NH₂ | 340 |
| 43 | CH₃ | 3,5-dibromo-2-hydroxyphenyl | NH₂ | 400 |

TABLE 1-continued

| Ex. | R¹ | R² | R³ | M/s [M + H]⁺ |
|---|---|---|---|---|
| 44 | CH₃ | (2-(pyrrolidin-1-yl)ethoxy)-bromo-fluoro-methylphenyl | NH₂ | 435 |
| 45 | CH₃ | (2-methoxyethoxy)-bromo-fluoro-methylphenyl | NH₂ | 396 |
| 46 | CH₃ | (2-hydroxyethoxy)-bromo-fluoro-methylphenyl | NH₂ | 382 |
| 47 | CH₃ | (2-hydroxyethoxy)-fluoro-methylphenyl | NH₂ | 304 |
| 48 | CH₃ | (3-hydroxypropoxy)-fluoro-methylphenyl | NH₂ | 317 |
| 49 | CH₃ | (2-methoxyethoxy)-fluoro-methylphenyl | NH₂ | 318 |
| 50 | CH₃ | (cyanomethoxy)-fluoro-methylphenyl | NH₂ | 299 |
| 51 | CH₃ | (2-(pyrrolidin-1-yl)ethoxy)-fluoro-methylphenyl | NH₂ | 357 |
| 52 | CH₃ | (2-(imidazol-1-yl)ethoxy)-fluoro-methylphenyl | NH₂ | 354 |
| 53 | CH₃ | (2-morpholinoethoxy)-fluoro-methylphenyl | NH₂ | 373 |
| 54 | CH₃ | (3-morpholinopropoxy)-fluoro-methylphenyl | NH₂ | 387 |
| 55 | CH₃ | (3-(4-methylpiperazin-1-yl)propoxy)-fluoro-methylphenyl | NH₂ | 400 |
| 56 | CH₃ | (2-hydroxyethoxy)-fluoro-methylphenyl | NH₂ | 304 |
| 57 | CH₃ | amino-fluoro-methylphenyl | NH₂ | 259 |
| 58 | CH₃ | (methylsulfonamido)-fluoro-methylphenyl | NH₂ | 337 |
| 59 | CH₃ | fluoro-methylphenyl | NHCH₃ | 258 |
| 60 | CH₃ | difluoro-methylphenyl | NH₂ | 262 |
| 61 | CH₃ | trifluoro-methylphenyl | NH₂ | 280 |
| 62 | CH₃ | chloro-methylthiophenyl | NH₂ | 266 |
| 63 | CH₃ | bromo-methyl-methoxyphenyl | NH₂ | 334 & 336 |

TABLE 1-continued
| Ex. | R¹ | R² | R³ | M/s [M+H]⁺ |
|---|---|---|---|---|
| 64 | CH₃ | 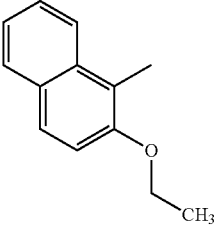 | NH₂ | 320 |
| 65 | CH₃ | 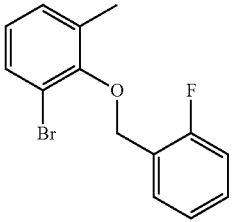 | NH₂ | 428 |
| 66 | CH₃ | 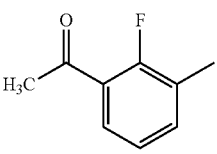 | NH₂ | 286 |
| 67 | CH₃ | 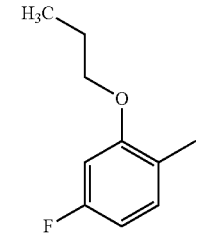 | NH₂ | 302 |
| 68 | CH₃ | 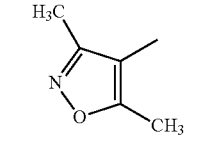 | NH₂ | 244 |
| 69 | CH₃ | 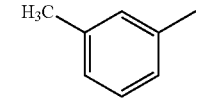 | NH₂ | 240 |
| 70 | CH₃ | 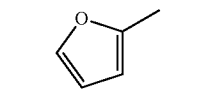 | NH₂ | 216 |
| 71 | CH₃ | 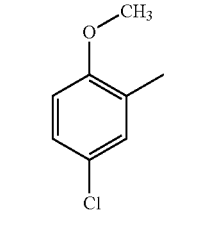 | NH₂ | 290 |
| 72 | CH₃ | 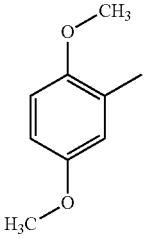 | NH₂ | 286 |
| 73 | CH₃ | 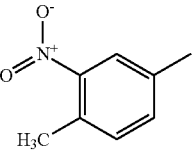 | NH₂ | 285 |
| 74 | CH₃ | 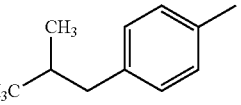 | NH₂ | 282 |
| 75 | CH₃ | 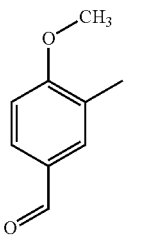 | NH₂ | 284 |
| 76 | CH₃ | 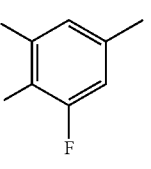 | NH₂ | 280 |
| 77 | CH₃ | 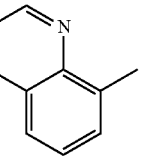 | NH₂ | 277 |
| 78 | CH₃ | 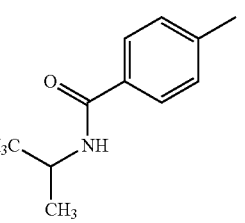 | NH₂ | 311 |
| 79 | CH₃ | 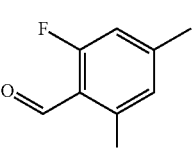 | NH₂ | 290 |

TABLE 1-continued

| Ex. | R¹ | R² | R³ | M/s [M + H]⁺ |
|---|---|---|---|---|
| 80 | CH₃ | 3-fluoro-5-methylphenoxyacetic acid | NH₂ | 318 |
| 81 | CH₃ | N-methyl-3-methylbenzamide | NH₂ | 283 |
| 82 | CH₃ | 5-methyl-2-(piperazin-1-yl)pyrimidine | NH₂ | 312 |
| 83 | CH₃ | 2,4-dimethoxy-5-methylpyrimidine | NH₂ | 288 |
| 84 | CH₃ | 3-methylbenzaldehyde | NH₂ | 254 |
| 85 | CH₃ | 2-methoxy-5-methylpyrimidine | NH₂ | 258 |
| 86 | CH₃ | N-isobutyl-3-methylbenzamide | NH₂ | 325 |
| 87 | CH₃ | N-methyl-3-methylbenzenesulfonamide | NH₂ | 319 |
| 88 | CH₃ | 4-methoxy-3-methyl-(trifluoromethyl)benzene | NH₂ | 324 |
| 89 | CH₃ | 2,4-dimethoxy-1-methylbenzene | NH₂ | 286 |
| 90 | CH₃ | 2,6-dimethoxy-1-methylbenzene | NH₂ | 286 |
| 91 | CH₃ | 2-methyl-4-(trifluoromethyl)phenol | NH₂ | 310 |
| 92 | CH₃ | 4-methylbenzene-1,3-diol | NH₂ | 258 |
| 93 | CH₃ | 4-chloro-2-methylphenol | NH₂ | 276 |
| 94 | CH₃ | 4-methoxy-3-methylbenzoic acid | NH₂ | 300 |
| 95 | CH₃ | 2,6-dichloro-4-methylphenol | NH₂ | 310 |
| 96 | CH₃ | 2-chloro-6-fluoro-4-methylphenol | NH₂ | 294 |

TABLE 1-continued

| Ex. | R¹ | R² | R³ | M/s [M + H]⁺ |
|---|---|---|---|---|
| 97 | CH₃ | 4-chloro-2-bromo-6-methylphenol | NH₂ | 353 & 356 |
| 98 | CH₃ | 2,4-difluoro-3-methoxy-5-methylphenyl | NH₂ | |
| 99 | CH₃ | N-isopropyl-4-methoxy-3-methylbenzamide | NH₂ | 341 |
| 100 | CH₃ | 4-hydroxy-3-methylbenzaldehyde | NH₂ | 270 |
| 101 | CH₃ | 2-amino-5-methyl-3-(trifluoromethyl)pyridine | NH₂ | 310 |
| 102 | CH₃ | 2,6-difluoro-4-methylbenzonitrile | NH₂ | 287 |
| 103 | CH₃ | N-(3-(dimethylamino)propyl)-4-methoxy-3-methylbenzylamine | NH₂ | 244 |
| 104 | CH₃ | (4-methoxy-3-methylphenyl)methanol | NH₂ | 286 |
| 105 | CH₃ | N-(3-fluoro-2-methoxy-5-methylphenyl)acetamide | NH₂ | 331 |
| 106 | CH₃ | 2,6-difluoro-4-methylbenzoic acid | NH₂ | 306 |
| 107 | CH₃ | 3-fluoro-2-hydroxy-5-methylbenzaldehyde | NH₂ | 288 |
| 108 | CH₃ | 2,6-difluoro-4-methylphenol | NH₂ | 278 |
| 109 | CH₃ | 3-fluoro-2-hydroxy-5-methylbenzonitrile | NH₂ | 285 |
| 110 | CH₃ | 4-fluoro-2-methoxy-1-methylbenzene | NH₂ | 274 |
| 111 | CH₃ | 2-hydroxy-4-methyl-6-(trifluoromethyl)phenyl | NH₂ | 310 |

TABLE 1-continued

| Ex. | R¹ | R² | R³ | M/s [M + H]⁺ |
|---|---|---|---|---|
| 112 | CH₃ | 2-methyl-6-fluorophenol | NH₂ | 260 |
| 113 | CH₃ | 2,4-dimethoxy-5-methylbenzenesulfonic acid | NH₂ | 336 |
| 114 | CH₃ | 5-chloro-2,4-dimethoxy-toluene | NH₂ | 320 |
| 115 | CH₃ | 2-chloro-6-(trifluoromethyl)-4-methylphenol | NH₂ | 344 |
| 116 | CH₃ | 2-(benzyloxy)-3-fluoro-N,N,5-trimethylbenzamide | NH₂ | 421 |
| 117 | CH₃ | 4-chloro-6-methylbenzene-1,3-diol | NH₂ | 292 |
| 118 | CH₃ | 2-chloro-6-methyl-4-(trifluoromethyl)-3-methoxyphenol | NH₂ | 358 |
| 119 | CH₃ | 2-bromo-4-chloro-6-methylbenzene-1,3-diol | NH₂ | 370 & 372 |
| 120 | CH₃ | 2,4-dimethoxy-5-methyl-N-methylbenzenesulfonamide | NH₂ | 379 |
| 121 | CH₃ | 2,4-dimethoxy-5-methyl-N-isopropylbenzenesulfonamide | NH₂ | 407 |
| 122 | CH₃ | 2-chloro-6-methyl-4-(trifluoromethyl)phenol | NH₂ | 344 & 346 |
| 123 | CH₃ | 2-methoxy-4-(trifluoromethoxy)toluene | NH₂ | 340 |
| 124 | CH₃ | 2-methyl-5-(trifluoromethoxy)phenol | NH₂ | 326 |
| 125 | CH₃ | 4-chloro-2-methoxy-5-(trifluoromethoxy)toluene | NH₂ | 374 |

TABLE 1-continued

| Ex. | R¹ | R² | R³ | M/s [M + H]⁺ |
|---|---|---|---|---|
| 126 | CH₃ | 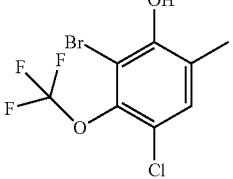 | NH₂ | 440 |
| 127 | CH₃ | 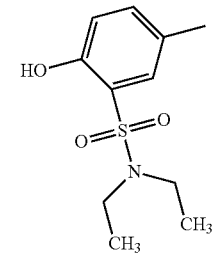 | NH₂ | 377 |
| 128 | CH₃ | 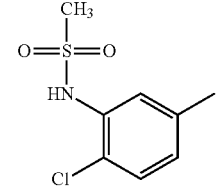 | NH₂ | 353 |
| 129 | CH₃ | 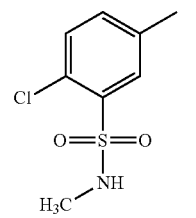 | NH₂ | 353 |
| 130 | CH₃ | 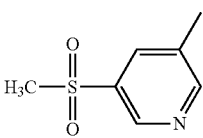 | NH₂ | 304 |
| 131 | CH₃ | 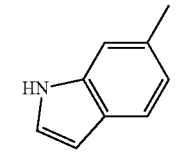 | NH₂ | 265 |
| 132 | CH₃ | 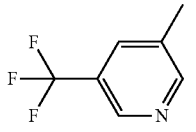 | NH₂ | 295 |

Further preferred compounds of the present invention are as shown in Table 2 below. The methods of preparation being described thereinafter.

TABLE 2

| Ex. | Chemical Structure | Compound name | M/s [M + H]⁺ |
|---|---|---|---|
| 2-1 | 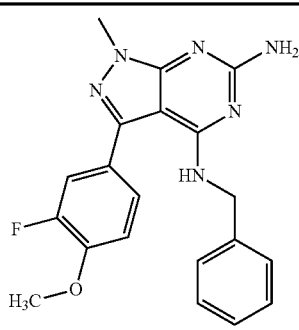 | N*4*-Benzyl-3-(3-fluoro-4-methoxy-phenyl)-1-methyl-1H-pyrazolo[3,4-d]pyrimidine-4,6-diamine | 379 |
| 2-2 | 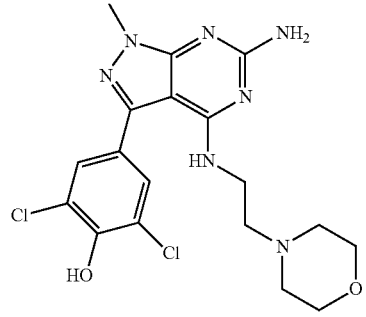 [SMILES: Cn1nc(-c2cc(Cl)c(O)c(Cl)c2)c2c(NCCN3CCOCC3)nc(N)nc21] | 4-[6-Amino-1-methyl-4-(2-morpholin-4-yl-ethylamino)-1H-pyrazolo[3,4-d]pyrimidin-3-yl]-2,6-dichloro-phenol | 438 & 440 |

General Conditions:

Mass spectra are run on an open access Waters 600/ZQ HPLC/Mass Spectrometer system using electrospray ionization. [M+H]⁺ refers to mono-isotopic molecular weights.

The invention is further illustrated by the following non-limiting examples, where the following abbreviations are employed:

THF is tetrahydrofuran, EtOAc is ethyl acetate, mCPBA is 3-chloroperoxybenzoic acid, DMF is N,N-dimethylformamide, DCM is dichloromethane, MeCN is acetonitrile, DPPF is 1,1'-bis(diphenylphosphino)ferrocine, DIAD is diisopropyl azodicarboxylate, $Et_3N$ is triethylamine, MeOH is methanol, EtOH is ethanol, $CHCl_3$ is chloroform, AcOH is acetic acid, $PCy_3$ is tricyclohexyl phosphine, $PPh_3$ is triphenylphosphine, DMSO is dimethyl sulfoxide, HPLC is high performance liquid chromatography, $MgSO_4$ is magnesium sulphate, NMP is 1-Methyl-2-pyrrolidinone, TFA is trifluoroacetic acid, DME is 1,2-dimethoxyethane, HATU is [Dimethylamino-([1,2,3]triazolo[4,5-b]pyridin-3-yloxy)-methylene]-dimethyl-ammonium; hexafluorophosphate, TMSCl is trimethylchlorosilane, $MP-BH_4$ is macroporous polystyrene borohydride, $Pd(dppf)Cl_2$ is [1,1'-bis(diphenyl phosphino)-ferrocenedichloro palladium(II), complex with dichloromethane, $Pd_2(dba)_3$ is tris(dibenzylileneacetone) di palladium(0), $Pd(PPh_3)_2Cl_2$ is bis(triphenylphosphine) palladium(II)dichloride, $Pd(PPh_3)_4$ is tetrakis(triphenylphosphine)palladium(0) and $MeNH_2$ is methylamine.

Example 1

3-(3-Fluoro-4-methoxy-phenyl)-1-methyl-1H-pyrazolo[3,4-d]pyrimidin-6-ylamine

Method A (From Intermediates 1 or 2)

3-(3-Fluoro-4-methoxy-phenyl)-1-methyl-6-methylsulfanyl-1H-pyrazolo[3,4-d]pyrimidine a) From Intermediate 1

3-Bromo-1-methyl-6-methylsulfanyl-1H-pyrazolo[3,4-d]pyrimidine (Intermediate 1) (1.2 g, 3.0 mmol) is dissolved in THF (50 ml), under an inert atmosphere of argon. To this is added $Pd(PPh_3)_2Cl_2$ (0.1 g, 0.15 mmol) and $PPh_3$ (0.023 g, 0.09 mmol) simultaneously. A solution of $Na_2CO_3$ (0.96 g, 9.1 mmol) dissolved in 5 ml of distilled water is added and the reaction mixture is stirred for 15 minutes at room temperature. 4-methoxy-3-fluoro boronic acid (0.51 g, 3.0 mmol) is added and resulting mixture is refluxed at 70° C. for 4 hours. The reaction mixture is diluted with water and the aqueous layer is extracted with DCM. The organic portion is washed with brine, dried over $Na_2SO_4$, filtered and concentrated in vacuo. Purification of the crude residue by flash chromatography on silica eluting with 20% EtOAc:iso-hexanes affords the title compound.

The chloro analogue of Intermediate 1 can also be used by an analogous process.

b) From Intermediate 2

Trifluoro-methanesulfonic acid 1-methyl-6-methylsulfanyl-1H-pyrazolo[3,4-d]pyrimidin-3-yl ester (Intermediate 2) (1.0 g, 3.0 mmol) is dissolved in THF (50 ml), under an inert atmosphere of argon. To this is added $Pd(PPh_3)_2Cl_2$ (0.1 g, 0.15 mmol) and $PPh_3$ (0.023 g, 0.09 mmol) simultaneously. A solution of $Na_2CO_3$ (0.96 g, 9.1 mmol) dissolved in 5 ml of distilled water is added and the reaction mixture is stirred for 15 minutes at room temperature. 4-methoxy-3-fluoro boronic acid (0.51 g, 3.0 mmol) is added and resulting mixture is refluxed at 70° C. for 4 hours. The reaction mixture is diluted with water and the aqueous layer is extracted with DCM. The organic portion is washed with brine, dried over $Na_2SO_4$, filtered and concentrated in vacuo. Purification of the crude residue by flash chromatography on silica eluting with residue is purified by flash column chromatography 20% EtOAc:iso-hexanes affords the title compound.

3-(3-Fluoro-4-methoxy-phenyl)-6-methanesulfonyl-1-methyl-1H-pyrazolo[3,4-d]pyrimidine 3-(3-Fluoro-4-methoxy-phenyl)-1-methyl-6-methylsulfanyl-1H-pyrazolo[3,4-d]pyrimidine (0.84 g, 2.7 mmol) is dissolved in dry DCM (30 ml). The reaction mixture is cooled to 0-5° C. (ice-bath) and mCPBA (1.42 g, 8.2 mmol) is added in small portions. The reaction mixture is stirred for 1 hour at room temperature, diluted with DCM (20 ml), washed with saturated $NaHCO_3$, brine, dried over $Na_2SO_4$, filtered and concentrated in vacuo. Purification of the crude residue by flash chromatography on silica eluting with 0.8% MeOH:$CHCl_3$ affords compound as a white solid.

3-(3-Fluoro-4-methoxy-phenyl)-1-methyl-1H-pyrazolo[3,4-d]pyrimidin-6-ylamine 3-(3-Fluoro-4-methoxy-phenyl)-6-methanesulfonyl-1-methyl-1H-pyrazolo[3,4-d]pyrimidine (0.8 g, 2.3 mmol) is dissolved in a saturated solution of ammonia in THF in an autoclave and the reaction mixture is stirred at room temperature for 2-18 hours. The solvent is removed in vacuo and the resulting solid is suspended in methanol, stirred at room temperature for 30 minutes and collected by filtration to afford the title compound as a white solid.

Method B From Intermediate 3

3-Bromo-1-methyl-1H-pyrazolo[3,4-d]pyrimidin-6-ylamine (Intermediate 3) (1.2 g, 5.2 mmol) is dissolved in THF (40 ml), under an inert atmosphere of argon. To this is added $Pd(PPh_3)_2Cl_2$ (0.224 g, 0.32 mmol), [3-fluoro-4-methoxyphenyl]boronic acid (0.98 g, 5.8 mmol) and a solution of $Na_2CO_3$ (1.5 g, 14 mmol) dissolved in distilled water (4 ml). The reaction mixture is heated to reflux at 70° C. for 24 hours. After cooling to room temperature the reaction mixture is pre-absorbed onto silica and purification by flash chromatography on silica eluting with iso-hexanes:EtOAc (2:1) affords the title compound as a solid.

Examples 2-34 are prepared from either Intermediate 1 or Intermediate 2 following method A, or from Intermediate 3 following method B using commercial or synthesized boronic acids/esters. The corresponding chloro intermediates may be used in place of bromo intermediates. These compounds namely, 3-(4-Ethoxy-3-fluoro-phenyl)-1-methyl-1H-pyrazolo[3,4-d]pyrimidin-6-ylamine (Example 2)

3-(3-Fluoro-4-isopropoxy-phenyl)-1-methyl-1H-pyrazolo[3,4-d]pyrimidin-6-ylamine (Example 3)

3-(4-Methoxy-phenyl)-1-methyl-1H-pyrazolo[3,4-d]pyrimidin-6-ylamine (Example 4)

3-(3-Chloro-4-methoxy-phenyl)-1-methyl-1H-pyrazolo[3,4-d]pyrimidin-6-ylamine (Example 5)

3-(3-Bromo-4-methoxy-phenyl)-1-methyl-1H-pyrazolo[3,4-d]pyrimidin-6-ylamine (Example 6)

3-(3-Chloro-4-isopropoxy-phenyl)-1-methyl-1H-pyrazolo[3,4-d]pyrimidin-6-ylamine (Example 7)

3-Benzo[1,3]dioxol-5-yl-1-methyl-1H-pyrazolo[3,4-d]pyrimidin-6-ylamine (Example 8)

3-(2,3-Dihydro-benzo[1,4]dioxin-6-yl)-1-methyl-1H-pyrazolo[3,4-d]pyrimidin-6-ylamine (Example 9)
1-Methyl-3-(3,4,5-trimethoxy-phenyl)-1H-pyrazolo[3,4-d]pyrimidin-6-ylamine (Example 10)
3-(3-Fluoro-phenyl)-1-methyl-1H-pyrazolo[3,4-d]pyrimidin-6-ylamine (Example 11)
3-(3,4-Difluoro-phenyl)-1-methyl-1H-pyrazolo[3,4-d]pyrimidin-6-ylamine (Example 12)
3-(3-Chloro-4-fluoro-phenyl)-1-methyl-1H-pyrazolo[3,4-d]pyrimidin-6-ylamine (Example 13)
3-(3,4-Dichloro-phenyl)-1-methyl-1H-pyrazolo[3,4-d]pyrimidin-6-ylamine (Example 14)
3-(3-Bromo-5-fluoro-phenyl)-1-methyl-1H-pyrazolo[3,4-d]pyrimidin-6-ylamine (Example 15)
3-(5-Fluoro-2-methoxy-phenyl)-1-methyl-1H-pyrazolo[3,4-d]pyrimidin-6-ylamine (Example 16)
3-(3,5-Difluoro-2-methoxy-phenyl)-1-methyl-1H-pyrazolo[3,4-d]pyrimidin-6-ylamine (Example 17)
3-(2,3-Dimethyl-1H-indol-5-yl)-1-methyl-1H-pyrazolo[3,4-d]pyrimidin-6-ylamine (Example 18)
3-(7-Fluoro-1H-indol-5-yl)-1-methyl-1H-pyrazolo[3,4-d]pyrimidin-6-ylamine (Example 19)
3-Benzofuran-6-yl-1-methyl-1H-pyrazolo[3,4-d]pyrimidin-6-ylamine (Example 20)
1-Methyl-3-(3-trifluoromethyl-phenyl)-1H-pyrazolo[3,4-d]pyrimidin-6-ylamine (Example 21)
1-[3-(6-Amino-1-methyl-1H-pyrazolo[3,4-d]pyrimidin-3-yl)-phenyl]-ethanone (Example 22)
3-(6-Amino-1-methyl-1H-pyrazolo[3,4-d]pyrimidin-3-yl)-benzonitrile (Example 23)
3-(3-Methanesulfonyl-phenyl)-1-methyl-1H-pyrazolo[3,4-d]pyrimidin-6-ylamine (Example 24)
N-[3-(6-Amino-1-methyl-1H-pyrazolo[3,4-d]pyrimidin-3-yl)-phenyl]methanesulfonamide (Example 25)
1-[4-(6-Amino-1-methyl-1H-pyrazolo[3,4-d]pyrimidin-3-yl)-phenyl]-ethanone (Example 26)
4-(6-Amino-1-methyl-1H-pyrazolo[3,4-d]pyrimidin-3-yl)-benzonitrile (Example 27)
1-Methyl-3-pyridin-4-yl-1H-pyrazolo[3,4-d]pyrimidin-6-ylamine (Example 28)
3-(2-Chloro-pyridin-4-yl)-1-methyl-1H-pyrazolo[3,4-d]pyrimidin-6-ylamine (Example 29)
3-(2-Methoxy-pyridin-4-yl)-1-methyl-1H-pyrazolo[3,4-d]pyrimidin-6-ylamine (Example 30)
1-Methyl-3-pyridin-3-yl-1H-pyrazolo[3,4-d]pyrimidin-6-ylamine (Example 31)
3-(6-Methoxy-pyridin-3-yl)-1-methyl-1H-pyrazolo[3,4-d]pyrimidin-6-ylamine (Example 32)
3-(5-Fluoro-6-methoxy-pyridin-3-yl)-1-methyl-1H-pyrazolo[3,4-d]pyrimidin-6-ylamine (Example 33)
1-[5-(6-Amino-1-methyl-1H-pyrazolo[3,4-d]pyrimidin-3-yl)-thiophen-2-yl]-ethanone (Example 34)

Example 35

3-(4-Benzyloxy-3-fluoro-phenyl)-1-methyl-1H-pyrazolo[3,4-d]pyrimidin-6-ylamine

3-Bromo-1-methyl-1H-pyrazolo[3,4-d]pyrimidin-6-ylamine (Intermediate 3) (0.33 g, 1.46 mmol) and 4-benzyloxy-3-fluoro phenylboronic acid (0.43 g, 1.75 mmol) are suspended in 1,4-dioxane (5 ml) in a microwave vial flushed with argon. A solution of $Cs_2CO_3$ (1.43 g, 4.38 mmol) in water (1.5 ml) is added followed by $Pd(PPh_3)_4$ (0.085 g, 0.073 mmol) and the reaction mixture is heated using microwave radiation at 150° C. for 0.5 hours. After cooling to room temperature the reaction mixture is diluted with EtOAc (100 ml) and washed with saturated $NaHCO_3$. The organic portion is dried over $MgSO_4$, filtered, concentrated in vacuo and the resulting crude solid is triturated with EtOAc (~20 ml) to afford the title compound as an off-white solid.

Example 36

4-(6-Amino-1-methyl-1H-pyrazolo[3,4-d]pyrimidin-3-yl)-2-fluoro-phenol 3-(4-Benzyloxy-3-fluoro-phenyl)-1-methyl-1H-pyrazolo[3,4-d]pyrimidin-6-ylamine (Example 35) (0.52 g, 1.49 mmol) is suspended in a mixture of EtOH and AcOH (5:1, 120 ml). The reaction mixture is degassed with argon before the addition of 10% palladium on activated charcoal (0.50 g) and 1,4-cyclohexadiene (1.4 ml, 14.88 mmol). The reaction mixture is heated at 80° C. overnight and filtered hot through Celite® (filter agent) washing copiously with MeOH (~300 ml). The solvents are removed in vacuo and the resulting residue is triturated with EtOAc (~20 ml) to afford the title compound as a white solid.

Examples 37-40

These compounds namely,
2-(6-Amino-1-methyl-1H-pyrazolo[3,4-d]pyrimidin-3-yl)-4-fluoro-phenol (Example 37)
3-(6-Amino-1-methyl-1H-pyrazolo[3,4-d]pyrimidin-3-yl)-5-fluoro-phenol (Example 38)
4-(6-Amino-1-methyl-1H-pyrazolo[3,4-d]pyrimidin-3-yl)-phenol (Example 39)
3-(6-Amino-1-methyl-1H-pyrazolo[3,4-d]pyrimidin-3-yl)-phenol (Example 40)
are prepared either from the phenol boronic acid/esters using standard Suzuki coupling methodology or from the benzyl protected phenol boronic acid/esters following a similar procedure described for Example 36.

Example 41

4-(6-Amino-1-methyl-1H-pyrazolo[3,4-d]pyrimidin-3-yl)-2-chloro-6-fluoro-phenol

3-Bromo-1-methyl-1H-pyrazolo[3,4-d]pyrimidin-6-ylamine (Intermediate 3) (0.125 g, 0.55 mmol), 2-Chloro-6-methoxy-4-(4,4,5,5-tetramethyl-1,3,2-dioxaborolan-2-yl) phenol (0.203 g, 0.712 mmol) and tetrakis(triphenylphosphine)palladium (0.038 g, 0.066 mmol) are added to 1,4-dioxane (3 ml) in a microwave vial and the mixture is sonicated. A solution of cesium carbonate (0.55 g, 3.29 mmol) in water (0.3 ml) is added and the reaction mixture is heated using microwave radiation at 150° C. for 30 minutes. The reaction mixture is filtered through Celite® (filter agent) washing with EtOAc, the filtrate is diluted with more EtOAc and washed with water and brine. The organic portion is dried over $MgSO_4$, filtered, concentrated in vacuo and purification of the crude residue by preparative HPLC (water/acetonitrile, 0.1% TFA) affords the title compound.

Example 42

4-(6-Amino-1-methyl-1H-pyrazolo[3,4-d]pyrimidin-3-yl)-2-bromo-6-fluoro-phenol

Example 42a

HBr Salt 4-(6-Amino-1-methyl-1H-pyrazolo[3,4-d]pyrimidin-3-yl)-2-fluoro-phenol (Example 36) (25 mg, 0.10 mmol) is suspended in glacial acetic acid (0.5 ml). Bromine (5 μL, 0.10 mmol) is added and the reaction mixture is stirred at room temperature overnight. The solvents are removed in vacuo to afford the title compound as the hydrobromide salt.

Example 42b

HCl Salt

A solution of crude 4-(6-amino-1-methyl-1H-pyrazolo[3,4-d]pyrimidin-3-yl)-2-bromo-6-fluoro-phenol hydrobromide (Example 42a) in methanol is converted to its free base by the addition of excess triethylamine. The resulting free base is purified by flash chromatography on silica using a solvent gradient of iso-hexanes:EtOAc (50% EtOAc to 100% EtOAc). The appropriate fraction are combined and concentrated in vacuo, the residue is treated with 4M hydrogen chloride (4M in 1,4-dioxane) and the solvent is removed in vacuo. The resulting hydrochloride salt is purified by reverse phase column chromatography (Isolute™ C18) eluting with water:acetonitrile to afford the title compound as the hydrochloride salt.

Example 43

4-(6-Amino-1-methyl-1H-pyrazolo[3,4-d]pyrimidin-3-yl)-2,6-dibromo-phenol 4-(6-Amino-1-methyl-1H-pyrazolo[3,4-d]pyrimidin-3-yl)-phenol (Example 39) (34 mg, 0.14 mmol) is suspended in glacial acetic acid (2.0 ml). Bromine (14 μL, 0.28 mmol) is added and the reaction mixture is then stirred at room temperature overnight. The solvents are removed in vacuo and purification of the crude residue by flash chromatography on silica using a solvent gradient of EtOAc:Et$_3$N (99:1) to remove non-polar impurities then eluting the product with EtOAc:MeOH:Et$_3$N (90:10:1) affords the title compound as a white solid.

Example 44

3-[3-Bromo-5-fluoro-4-(2-pyrrolidin-1-yl-ethoxy)-phenyl]-1-methyl-1H-pyrazolo[3,4-d]pyrimidin-6-ylamine 4-(6-Amino-1-methyl-1H-pyrazolo[3,4-d]pyrimidin-3-yl)-2-bromo-6-fluoro-phenol hydrochloride (Example 42b) (30 mg, 0.08 mmol) is dissolved in anhydrous THF (10 ml), K$_2$CO$_3$ (12 mg, 0.09 mmol) is added and the reaction mixture is stirred at room temperature for 10 minutes. Triphenylphosphine (116 mg, 0.44 mmol), DIAD (0.076 ml, 0.40 mmol) and 1-(2-hydroxyethyl)pyrrolidine (0.048 ml, 0.40 mmol) are added and the reaction mixture is heated to reflux for 20 hours. After cooling to room temperature the reaction mixture is diluted with water (~15 ml) and extracted with EtOAc (3×50 ml). The combined organic portions are dried over MgSO$_4$, filtered and concentrated in vacuo Purification of the crude residue by flash chromatography on silica firstly eluting the non-polar impurities with iso-hexanes:EtOAc (4:1 to 1:4) then eluting the product with EtOAc:MeOH:Et3N (4:1:0.01) affords the title compound.

Example 45

3-[3-Bromo-5-fluoro-4-(2-methoxy-ethoxy)-phenyl]-1-methyl-1H-pyrazolo[3,4-d]pyrimidin-6-ylamine 4-(6-Amino-1-methyl-1H-pyrazolo[3,4-d]pyrimidin-3-yl)-2-bromo-6-fluoro-phenol hydrochloride (Example 42b) (30 mg, 0.08 mmol) is dissolved in DMF (1 ml) then treated with K$_2$CO$_3$ (24 mg, 0.18 mmol) and 2-bromoethyl methyl ether (7.5 μL, 0.08 mmol). The reaction mixture is heated at 120° C. for 3 hours then cooled to room temperature, diluted with MeOH and concentrated in vacuo. The crude residue is dry loaded onto silica and purification by flash chromatography on silica eluting with iso-hexanes:EtOAc (50% EtOAc to 100% EtOAc) affords the title compound as an off-white soild.

Example 46

2-[4-(6-Amino-1-methyl-1H-pyrazolo[3,4-d]pyrimidin-3-yl)-2-bromo-6-fluoro-phenoxy]-ethanol 4-(6-Amino-1-methyl-1H-pyrazolo[3,4-d]pyrimidin-3-yl)-2-bromo-6-fluoro-phenol hydrochloride (Example 42b) (30 mg, 0.08 mmol) is dissolved in DMF (1 ml) then treated with K$_2$CO$_3$ (24 mg, 0.18 mmol) and 2-bromoethanol (5.7 μL, 0.08 mmol). The reaction mixture is heated at 120° C. for 3 hours then cooled to room temperature, diluted with MeOH and concentrated onto silica. Purification by flash column chromatography on silica using iso-hexanes:EtOAc (50% EtOAc to 100% EtOAc) followed by recrystallisation from MeOH afforded the title compound as an off-white solid.

Examples 47-56 are prepared analogously to Example 46 from the corresponding phenols and halogenated intermediates.
These compounds namely,
2-[4-(6-Amino-1-methyl-1H-pyrazolo[3,4-d]pyrimidin-3-yl)-2-fluoro-phenoxy]-ethanol (Example 47)
3-[4-(6-Amino-1-methyl-1H-pyrazolo[3,4-d]pyrimidin-3-yl)-2-fluoro-phenoxy]-propan-1-ol (Example 48)
3-[3-Fluoro-4-(2-methoxy-ethoxy)phenyl]-1-methyl-1H-pyrazolo[3,4-d]pyrimidin-6-ylamine (Example 49)
[4-(6-Amino-1-methyl-1H-pyrazolo[3,4-d]pyrimidin-3-yl)-2-fluoro-phenoxy]-acetonitrile (Example 50)
3-[3-Fluoro-4-(2-pyrrolidin-1-yl-ethoxy)phenyl]-1-methyl-1H-pyrazolo[3,4-d]pyrimidin-6-ylamine (Example 51)
3-[3-Fluoro-4-(2-imidazol-1-yl-ethoxy)-phenyl]-1-methyl-1H-pyrazolo[3,4-d]pyrimidin-6-ylamine (Example 52)
3-[3-Fluoro-4-(2-morpholin-4-yl-ethoxy)phenyl]-1-methyl-1H-pyrazolo[3,4-d]pyrimidin-6-ylamine (Example 53)
3-[3-Fluoro-4-(3-morpholin-4-yl-propoxy)-phenyl]-1-methyl-1H-pyrazolo[3,4-d]pyrimidin-6-ylamine (Example 54)
3-{3-Fluoro-4-[3-(4-methyl-piperazin-1-yl)-propoxy]-phenyl}-1-methyl-1H-pyrazolo[3,4-d]pyrimidin-6-ylamine (Example 55)
2-[2-(6-Amino-1-methyl-1H-pyrazolo[3,4-d]pyrimidin-3-yl)-4-fluoro-phenoxy]-ethanol (Example 56)

Example 57

3-(4-Amino-3-fluoro-phenyl)-1-methyl-1H-pyrazolo[3,4-d]pyrimidin-6-ylamine

3-Chloro-1-methyl-1H-pyrazolo[3,4-d]pyrimidin-6-ylamine (Intermediate 4) (1.2 g, 5.2 mmol) is dissolved in THF (40 ml) under an inert atmosphere of argon. To this is added Pd(PPh$_3$)$_2$Cl$_2$ (0.224 g, 0.32 mmol), [3-fluoro-4-methoxyphenyl]boronic acid (0.98 g, 5.8 mmol) and a solution of Na$_2$CO$_3$ (1.5 g, 14 mmol) dissolved in distilled water (4 ml). The reaction mixture is heated to reflux at 70° C. for 24 hours. The reaction mixture is absorbed on silica and purification by flash column chromatography on silica eluting with 2:1 isohexanes: EtOAc affords the title compound.

Example 58

N-[4-(6-Amino-1-methyl-1H-pyrazolo[3,4-d]pyrimidin-3-yl)-2-fluoro-phenyl]methanesulfonamide 3-(4-Amino-3-fluoro-phenyl)-1-methyl-1H-pyrazolo[3,4-d]pyrimidin-6-ylamine (Example 58) (0.13 g, 0.50 mmol) is dissolved in pyridine (1.5 ml) under an inert atmosphere of argon. The reaction mixture is cooled to −10° C. (dry ice/acetone bath) then methanesulfonyl chloride (0.078 ml, 0.75 mmol) is added drop wise over a period of 15 minutes. The reaction mixture is stirred at −10° C. for 30 minutes then allowed to warm to room temperature and stirred for further 3 hours. The reaction mixture is diluted with EtOAc (100 ml) and washed with water (3×40 ml) and brine (10 ml). The organic portion is dried over $MgSO_4$, filtered and concentrated in vacuo. The resulting solid is triturated with hot EtOAc (plus few drops of MeOH), filtered and dried under vacuum at 50° C. for 3 hours to afford the title compound as an off-white solid.

Example 59

[3-(3-Fluoro-4-methoxy-phenyl)-1-methyl-1H-pyrazolo[3,4-d]pyrimidin-6-yl]-methyl-amine This compound is prepared analogously to Example 1, Method A by replacing ammonia in the final step with methylamine to afford the title compound.

Example 60

3-(3,5-Difluoro-phenyl)-1-methyl-1H-pyrazolo[3,4-d]pyrimidin-6-ylamine

3-Bromo-1-methyl-1H-pyrazolo[3,4-d]pyrimidin-6-ylamine (Intermediate 3) (0.05 g, 0.22 mmol) is suspended in 1,4-dioxane (1 ml). The reaction mixture is sonicated to give a very fine suspension and placed in a microwave vial containing 3,5-difluoro phenylboronic acid (38 mg, 0.24 mmol). To this is added a solution of tris(dibenzylileneacetone) di palladium(0) (0.002 g, 0.0022 mmol) in 1,4-dioxane (0.5 ml) followed by a solution of tricyclohexyl phosphine (0.0015 g, 0.0053 mmol) in 1,4-dioxane (0.5 ml) and 1.27M aqueous potassium phosphate solution (0.294 ml, 0.374 mmol). The resulting mixture is flushed with argon and heated using microwave radiation at 150° C. for 30 minutes. The reaction mixture is treated with DMSO (2 ml) and filtered through a 2 g silica cartridge washing with EtOAc:MeOH (10:1, 4 ml). The filtrate is concentrated in vacuo and the resulting residue is dissolved in NMP (4 ml) and loaded onto an Isolute™ SCX column (silica based cation exchange sorbent) eluting with MeOH (4 ml) and 1M $NH_3$ in MeOH (6 ml). The appropriate fractions are combined and concentrated in vacuo to afford the title compound.

Examples 61-77 are prepared analogously to Example 60 from the appropriate commercial boronic acids using standard Suzuki coupling methodology. Examples 61-65 are further purified by preparative HPLC (water/acetonitrile, 0.1% TFA) to afford the products as the trifluoroacetate salts.

These compounds namely,
1-Methyl-3-(2,3,4-trifluoro-phenyl)-1H-pyrazolo[3,4-d]pyrimidin-6-ylamine trifluoroacetate (Example 61)
3-(5-Chloro-thiophen-2-yl)-1-methyl-1H-pyrazolo[3,4-d]pyrimidin-6-ylamine trifluoroacetate (Example 62)
3-(5-Bromo-2-methoxy-phenyl)-1-methyl-1H-pyrazolo[3,4-d]pyrimidin-6-ylamine trifluoroacetate (Example 63)
3-(2-Ethoxy-naphthalen-1-yl)-1-methyl-1H-pyrazolo[3,4-d]pyrimidin-6-ylamine trifluoroacetate (Example 64)
3-[3-Bromo-2-(2-fluoro-benzyloxy)-phenyl]-1-methyl-1H-pyrazolo[3,4-d]pyrimidin-6-ylamine trifluoroacetate (Example 65)
1-[3-(6-Amino-1-methyl-1H-pyrazolo[3,4-d]pyrimidin-3-yl)-2-fluoro-phenyl]-ethanone (Example 66)
3-(4-Fluoro-2-propoxy-phenyl)-1-methyl-1H-pyrazolo[3,4-d]pyrimidin-6-ylamine (Example 67)
3-(3,5-Dimethyl-isoxazol-4-yl)-1-methyl-1H-pyrazolo[3,4-d]pyrimidin-6-ylamine (Example 68)
1-Methyl-3-m-tolyl-1H-pyrazolo[3,4-d]pyrimidin-6-ylamine (Example 69)
3-Furan-2-yl-1-methyl-1H-pyrazolo[3,4-d]pyrimidin-6-ylamine (Example 70)
3-(5-Chloro-2-methoxy-phenyl)-1-methyl-1H-pyrazolo[3,4-d]pyrimidin-6-ylamine (Example 71)
3-(2,5-Dimethoxy-phenyl)-1-methyl-1H-pyrazolo[3,4-d]pyrimidin-6-ylamine (Example 72)
1-Methyl-3-(4-methyl-3-nitro-phenyl)-1H-pyrazolo[3,4-d]pyrimidin-6-ylamine (Example 73)
3-(4-Isobutyl-phenyl)-1-methyl-1H-pyrazolo[3,4-d]pyrimidin-6-ylamine (Example 74)
3-(6-Amino-1-methyl-1H-pyrazolo[3,4-d]pyrimidin-3-yl)-4-methoxy-benzaldehyde (Example 75)
1-Methyl-3-(3,4,5-trifluoro-phenyl)-1H-pyrazolo[3,4-d]pyrimidin-6-ylamine (Example 76)
1-Methyl-3-quinolin-8-yl-1H-pyrazolo[3,4-d]pyrimidin-6-ylamine (Example 77)

Example 78

3-(6-Amino-1-methyl-1H-pyrazolo[3,4-d]pyrimidin-3-yl)-N-isopropyl-benzamide 3-(N-isopropylaminocarbonyl)benzene boronic acid (0.99 g, 0.48 mmol) and 1.27M aqueous potassium phosphate solution (0.591 ml, 0.75 mmol) are stirred in 1,4-dioxane (1 ml), under an inert atmosphere of argon for 15 minutes. Separately, 3-Bromo-1-methyl-1H-pyrazolo[3,4-d]pyrimidin-6-ylamine (Intermediate 3) (0.1 g, 0.44 mmol), $PCy_3$ (4 mg, 0.012 mmol) and $Pd_2(dba)_3$ (5 mg, 0.005 mmol) are stirred in 1,4-dioxane (1 ml) before being added to the boronic acid solution. The reaction mixture is heated to 100° C. for 1.5 hours and then filtered hot to remove the palladium residues. The filtrate is diluted with a little MeOH/water and the resulting precipitate is collected by filtration and dried under vacuum at 45° C. to afford the title compound.

Example 79-87 are prepared analogously to Example 78 from commercial or prepared boronic acids using standard Suzuki coupling methodology. The compounds are recovered from reaction mixtures and purified using conventional techniques such as, for example, flash chromatography, reverse phase chromatography or preparative HPLC. These compounds namely,
4-(6-Amino-1-methyl-1H-pyrazolo[3,4-d]pyrimidin-3-yl)-2,6-difluoro-benzaldehyde (Example 79)
[3-(6-Amino-1-methyl-1H-pyrazolo[3,4-d]pyrimidin-3-yl)-5-fluoro-phenoxy]-acetic acid (Example 80)

3-(6-Amino-1-methyl-1H-pyrazolo[3,4-d]pyrimidin-3-yl)-N-methyl-benzamide (Example 81)
1-Methyl-3-(2-piperazin-1-yl-pyrimidin-5-yl)-1H-pyrazolo[3,4-d]pyrimidin-6-ylamine (Example 82)
3-(2,4-Dimethoxy-pyrimidin-5-yl)-1-methyl-1H-pyrazolo[3,4-d]pyrimidin-6-ylamine (Example 83)
3-(6-Amino-1-methyl-1H-pyrazolo[3,4-d]pyrimidin-3-yl)-benzaldehyde (Example 84)
3-(2-Methoxy-pyrimidin-5-yl)-1-methyl-1H-pyrazolo[3,4-d]pyrimidin-6-ylamine (Example 85)
3-(6-Amino-1-methyl-1H-pyrazolo[3,4-d]pyrimidin-3-yl)-N-isobutyl-benzamide (Example 86)
3-(6-Amino-1-methyl-1H-pyrazolo[3,4-d]pyrimidin-3-yl)-N-methyl-benzenesulfonamide (Example 87)

Example 88

3-(2-Methoxy-5-trifluoromethyl-phenyl)-1-methyl-1H-pyrazolo[3,4-d]pyrimidin-6-ylamine 3-Bromo-1-methyl-1H-pyrazolo[3,4-d]pyrimidin-6-ylamine (Intermediate 3) (0.1 g, 0.44 mmol), 2-methoxy-5-trifluoromethylphenylboronic acid (0.116 g, 0.53 mmol), Pd(dppf)Cl$_2$ (0.032 g, 0.044 mmol), DME (4 ml) and 2M aqueous Na$_2$CO$_3$, are mixed together and heated using microwave radiation at 100° C. for 30 minutes. The reaction mixture is diluted with EtOAc (30 mls), MgSO$_4$ is added and the resulting mixture is filtered through Celite® (filter agent), washing with EtOAc. The reaction mixture is absorbed onto silica and purification by flash chromatography on silica eluting with DCM then MeOH:DCM (5:95) affords the title compound.

Example 89 and 90 are prepared analogously to Example 88 from commercial boronic acids using standard Suzuki coupling methodology. These compounds namely,
3-(2,4-Dimethoxy-phenyl)-1-methyl-1H-pyrazolo[3,4-d]pyrimidin-6-ylamine (Example 89)
3-(2,6-Dimethoxy-phenyl)-1-methyl-1H-pyrazolo[3,4-d]pyrimidin-6-ylamine (Example 90)

Example 91

2-(6-Amino-1-methyl-1H-pyrazolo[3,4-d]pyrimidin-3-yl)-4-trifluoromethyl-phenol

To a solution of 3-(2-Methoxy-5-trifluoromethyl-phenyl)-1-methyl-1H-pyrazolo[3,4-d]pyrimidin-6-ylamine (Example 88) (0.08 g, 0.25 mmol) in DCM (5 ml) is added drop wise boron tribromide (1M solution in DCM, 0.99 ml, 0.99 mmol), under an inert atmosphere of argon at 0-5° C. (icebath). The reaction mixture is warmed to room temperature, stirred for 2 hours and then quenched with water (10 ml). The resulting solid is collected by filtration and dried under vacuum to afford the title compound.

Example 92

4-(6-Amino-1-methyl-1H-pyrazolo[3,4-d]pyrimidin-3-yl)-benzene-1,3-diol

This compound is prepared analogously to Example 91 by replacing 3-(2-Methoxy-5-trifluoromethyl-phenyl)-1-methyl-1H-pyrazolo[3,4-d]pyrimidin-6-ylamine phenyl) (Example 88) with 3-(2,4-Dimethoxy-phenyl)-1-methyl-1H-pyrazolo[3,4-d]pyrimidin-6-ylamine (Example 89). The addition of water during the aqueous quench results in a precipitate but on filtration a gum forms, this gum is therefore triturated with diethyl ether (50 ml) to form a solid, which is collected by filtration and dried under vacuum to afford the title compound.

Example 93

2-(6-Amino-1-methyl-1H-pyrazolo[3,4-d]pyrimidin-3-yl)-4-chloro-phenol

This compound is prepared analogously to Example 91 by replacing 3-(2-Methoxy-5-trifluoromethyl-phenyl)-1-methyl-1H-pyrazolo[3,4-d]pyrimidin-6-ylamine (Example 88) with 3-(5-Chloro-2-methoxy-phenyl)-1-methyl-1H-pyrazolo[3,4d]pyrimidin-6-ylamine (Example 71) to afford the title compound.

Example 94

3-(6-Amino-1-methyl-1H-pyrazolo[3,4-d]pyrimidin-3-yl)-4-methoxy-benzoic acid 3-(6-Amino-1-methyl-1H-pyrazolo[3,4-d]pyrimidin-3-yl)-4-methoxy-benzaldehyde (Example 75) (0.5 g, 1.77 mmol) is suspended in t-butanol (12 ml) and 2-methyl-2-butene (0.562 ml, 5.31 mmol). To this is added a solution of sodium chlorite (0.367 g, 4.06 mmol) and sodium dihydrogen phosphate (0.848 g, 7.06 mmol) in water (5 ml). The reaction mixture is stirred at room temperature for 48 hours and the resulting precipitate is collected by filtration, dissolved in saturated aqueous NaHCO$_3$ (100 ml) and washed with EtOAc (2×50 ml). The aqueous portion is acidified to pH1 with 2M HCl resulting in an off-white solid which is collected by filtration and dried under vacuum for 72 hours to afford the title compound.

Example 95

4-(6-Amino-1-methyl-1H-pyrazolo[3,4-d]pyrimidin-3-yl)-2,6-dichloro-phenol

Step 1: 3-(4-Benzyloxy-3,5-dichloro-phenyl)-1-methyl-1H-pyrazolo[3,4-d]pyrimidin-6-ylamine This compound is prepared analogously to Example 78 by replacing 3-(N-isopropylaminocarbonyl)benzene boronic acid with 4-(benzyloxy)-3,5 dichlorophenyl boronic acid to afford the title compound.

Step 2: 4-(6-Amino-1-methyl-1H-pyrazolo[3,4-d]pyrimidin-3-yl)-2,6-dichloro-phenol 3-(4-Benzyloxy-3,5-dichloro-phenyl)-1-methyl-1H-pyrazolo[3,4-d]pyrimidin-6-ylamine (0.2 g, 0.500 mmol) is dissolved in 48% HBr in water (20 ml) and heated to 120° C. for 1 hour. The reaction mixture is cooled to room temperature and the resulting precipitate is collected by filtration and re-crystallised from EtOH to afford the title compound.

Example 96

4-(6-Amino-1-methyl-1H-pyrazolo[3,4-d]pyrimidin-3-yl)-2-chloro-6-fluoro-phenol

This compound is prepared analogously to Example 78 by replacing 3-(N-isopropylamino carbonyl)benzene boronic acid with 3-Chloro-5-fluoro-4-hydroxyphenyl-boronic acid (Intermediate 8). The reaction is carried out using microwave radiation at 150° C. for 30 minutes.

Example 97

2-(6-Amino-1-methyl-1H-pyrazolo[3,4-d]pyrimidin-3-yl)-6-bromo-4-chloro-phenol

Step 1: 3-(5-Chloro-2-methoxy-phenyl)-1-methyl-4,5-dihydro-1H-pyrazolo[3,4-d]pyrimidin-6-ylamine trifluoroacetate 3-(5-Chloro-2-methoxy-phenyl)-1-methyl-1H-pyrazolo[3,4-d]pyrimidin-6-ylamine (Example 71) is dissolved in MeOH (3 ml) and THF (5 ml). To this is added NaBH$_4$ (0.522 g, 13.8 mmol), and the reaction mixture is stirred at room temperature until no more gas is given off. After 30 minutes the reaction mixture is filtered through Celite® (filter agent), washing with MeOH. The filtrate is concentrated in vacuo and the resulting residue is diluted with EtOAc and washed with water. The organic portion is dried over MgSO$_4$, filtered, concentrated in vacuo and purification of the crude residue by preparative HPLC (water/acetonitrile, 0.1% TFA) affords the title compound as the trifluoroacetate salt.

Step 2: 2-(6-Amino-1-methyl-1H-pyrazolo[3,4-d]pyrimidin-3-yl)-6-bromo-4-chloro-phenol 3-(5-Chloro-2-methoxy-phenyl)-1-methyl-4,5-dihydro-1H-pyrazolo[3,4-d]pyrimidin-6-ylamine trifluoroacetate is dissolved in 48% HBr in water (10 ml) and heated using microwave radiation at 120° C. for 2 hours. Purification of the reaction mixture by preparative HPLC (water/acetonitrile, 0.1% TFA) affords the title compound as the minor product of the reaction as the trifluoroacetate salt.

Example 98

3-(3,5-Difluoro-4-methoxy-phenyl)-1-methyl-1H-pyrazolo[3,4-d]pyrimidin-6-ylamine This compound is prepared analogously to Example 78 by replacing 3-(N-isopropylamino carbonyl)benzene boronic acid with 3,5-Difluoro-4-methoxy-phenyl-boronic acid (Intermediate 9) to afford the title compound.

Example 99

3-(6-Amino-1-methyl-1H-pyrazolo[3,4-d]pyrimidin-3-yl)-N-isopropyl-4-methoxy-benzamide 3-(6-Amino-1-methyl-1H-pyrazolo[3,4-d]pyrimidin-3-yl)-4-methoxy-benzoic acid (Example 94) (0.075 g, 0.25 mmol) is dissolved in DMF (5 ml), HATU (0.095 g, 0.25 mmol) is then added followed by N-Methylmorpholine (0.110 ml, 1.0 mmol) and isopropylamine (0.022 ml, 0.25 mmol) and the reaction mixture is stirred at room temperature for 15 hours. The solvent is removed in vacuo and the residue is diluted with water (3 ml) and left to stand for 3 hours. The resulting solid precipitate is collected by filtration, washed with a further 5 ml of water and dried under vacuum to afford the title compound.

Example 100

3-(6-Amino-1-methyl-1H-pyrazolo[3,4-d]pyrimidin-3-yl)-4-hydroxy-benzaldehyde

This compound is prepared analogously to Example 91 by replacing 3-(2-Methoxy-5-trifluoromethyl-phenyl)-1-methyl-1H-pyrazolo[3,4-d]pyrimidin-6-ylamine (Example 88) with 3-(6-Amino-1-methyl-1H-pyrazolo[3,4-d]pyrimidin-3-yl)-4-methoxy-benzaldehyde (Example 75) to afford the title compound.

Example 101

3-(6-Amino-5-trifluoromethyl-pyridin-3-yl)-1-methyl-1H-pyrazolo[3,4-d]pyrimidin-6-ylamine 3-Bromo-1-methyl-1H-pyrazolo[3,4-d]pyrimidin-6-ylamine (Intermediate 3) (0.1 g, 0.438 mmol), tetrakis(triphenylphosphine)palladium (0.031 g, 0.027 mmol), 5-(4,4,5,5-tetra methyl-[1,3,2]dioxaborolan-2-yl)-3-trifluoromethyl-pyridin-2-ylamine (Intermediate 10) (0.135 g, 0.669 mmol), cesium carbonate (0.290 g, 0.892 mmol) and water (1 ml) are suspended in 1,4-dioxane (4 ml) and heated using microwave radiation at 150° C. for 45 minutes. The reaction mixture is cooled to room temperature, filtered through Celite® (filter agent) and washed with EtOAc. The solvents are removed in vacuo and purification of the crude residue by flash chromatography on silica eluting with iso-hexanes:EtOAc (2:1) results in an off white solid. The solid is further purified by recrystallisation from 1:1 MeOH/EtOAc resulting in a white solid which is collected by filtration and dried under vacuum to afford the title compound.

Example 102

4-(6-Amino-1-methyl-1H-pyrazolo[3,4-d]pyrimidin-3-yl)-2,6-difluoro-benzonitrile

This compound is prepared analogously to Example 101 by replacing 5-(4,4,5,5-Tetramethyl-[1,3,2]dioxaborolan-2-yl)-3-trifluoromethyl-pyridin-2-ylamine (Intermediate 10) with 2,6-difluoro-4-(4,4,5,5-tetramethyl-[1,3,2]dioxaborolan-2-yl)-benzonitrile (Intermediate 11). Purification by preparative HPLC (water/acetonitrile, 0.1% TFA) affords the title compound as the trifluoroacetate salt.

Example 103

N-[3-(6-Amino-1-methyl-1H-pyrazolo[3,4-d]pyrimidin-3-yl)-4-methoxy-phenyl]-N',N'-dimethyl-propane-1,3-diamine 3-(6-Amino-1-methyl-1H-pyrazolo[3,4-d]pyrimidin-3-yl)-4-methoxy-benzaldehyde (Example 75) (0.06 g, 0.212 mmol) is suspended in THF (2 ml) and AcOH (0.2 ml). N,N-dimethyl-propane-1,3-diamine (0.0029 ml, 0.233 mmol) is added and reaction mixture is stirred for 1 hour 30 minutes at room temperature. After this time MP-BH$_4$ (3.2 mmol loading, 0.07 g, 0.225 mmol) is added and the mixture is continued to stir for a further 48 hours. The reaction mixture is filtered, washing with MeOH and the filtrate is concentrated in vacuo. Purification of the crude residue by preparative HPLC (water/acetonitrile, 0.5% TFA) affords the title compound as the trifluoroacetate salt.

Example 104

[3-(6-Amino-1-methyl-1H-pyrazolo[3,4-d]pyrimidin-3-yl)-4-methoxy-phenyl]-methanol 3-(6-Amino-1-methyl-1H-pyrazolo[3,4-d]pyrimidin-3-yl)-4-methoxy-benzaldehyde (Example 75) (0.040 g, 0.141 mmol) is suspended in dry MeOH (2.5 ml) and THF (1 ml). The reaction mixture is cooled to 0-5° C. (ice-bath) and sodium borohydride (0.006 g, 0.1551 mmol) is cautiously added. The reaction mixture is stirred at room temperature for 24 hours, filtered, washing with MeOH and concentrated in vacuo. The resulting solid is triturated in MeOH (minimal) and collected by filtration to afford the title compound as an off-white solid.

Example 105

N-[5-(6-Amino-1-methyl-1H-pyrazolo[3,4-d]pyrimidin-3-yl)-3-fluoro-2-methoxy-phenyl]-acetamide This compound is prepared analogously to Example 78 by replacing 4-(N-isopropylamino carbonyl)phenylboronic acid with N-[3-Fluoro-2-methoxy-5-(4,4,5,5-tetramethyl-[1,3,2]dioxaborolan-2-yl)-phenyl]-acetamide (Intermediate 12) to afford the title compound.

Example 106

4-(6-Amino-1-methyl-1H-pyrazolo[3,4-d]pyrimidin-3-yl)-2,6-difluoro-benzoic acid 4-(6-Amino-1-methyl-1H-pyrazolo[3,4-d]pyrimidin-3-yl)-2,6-difluoro-benzaldehyde (Example 79) (0.103 g, 0.345 mmol) is suspended in 2M NaOH (0.431 ml, 0.862 mmol), 35% $H_2O_2$ in water (17.3 ml, 17.025 mmol) is added and the reaction mixture is stirred at room temperature for 56 hours. The reaction mixture is filtered through filter paper, ice is added to the filtrate and the mixture is quenched with 5M HCl resulting in a white precipitate after 1.5 hours. This solid is collected by filtration, washed with water and dried under vacuum for 24 hours at 45° C. to afford the title compound.

Example 107

5-(6-Amino-1-methyl-1H-pyrazolo[3,4-d]pyrimidin-3-yl)-3-fluoro-2-hydroxy-benzaldehyde 4-(6-Amino-1-methyl-1H-pyrazolo[3,4-d]pyrimidin-3-yl)-2-fluoro-phenol (Example 36) (0.101 g, 0.268 mmol) is suspended in AcOH (2 ml) and hexamethylenetetriamine (0.267 g, 1.90 mmol) is added. The reaction mixture is heated to 90° C. (mixture solubilises at this temperature) for 6 hours, then cooled to room temperature and left overnight. The reaction mixture is concentrated in vacuo to a brown residue which is diluted with 5M HCl (2.5 ml), heated to 110° C. for 30 minutes, then poured onto ice/water. The resulting solid is removed by filtration and washed with water. The aqueous portion is concentrated in vacuo and purification of the crude residue by preparative HPLC (water/acetonitrile, 0.1% TFA) affords the title compound as the trifluoroacetate salt.

Example 108

4-(6-Amino-1-methyl-1H-pyrazolo[3,4-d]pyrimidin-3-yl)-2,6-difluoro-phenol 3-(3,5-Difluoro-4-methoxy-phenyl)-1-methyl-1H-pyrazolo[3,4-d]pyrimidin-6-ylamine (Example 98) (0.1 g, 0.342 mmol) is dissolved in 48% HBr in water (5 ml) and heated using microwave radiation at 120° C. for 30 minutes. Purification of the reaction mixture by preparative HPLC (water/acetonitrile, 0.1% TFA) affords the title compound as a white solid.

Example 109

5-(6-Amino-1-methyl-1H-pyrazolo[3,4-d]pyrimidin-3-yl)-3-fluoro-2-hydroxy-benzonitrile 4-(6-Amino-1-methyl-1H-pyrazolo[3,4-d]pyrimidin-3-yl)-2-bromo-6-fluoro-phenol hydrobromide (Example 42a) (0.07 g, 0.167 mmol), $Zn(CN)_2$ (0.020 g, 0.167 mmol), $Pd_2(dba)_3$ (0.076 g, 0.08 mmol) and DPPF (0.092 g, 0.167 mmol) are dissolved in DMF (2.5 ml) and heated to 180° C. for 40 minutes. The reaction mixture is flitered through Celite® (filter agent) washing with MeOH, the filtrate is concentrated in vacuo and purification of the resulting residue is by preparative HPLC (water/acetonitrile, 0.1% TFA) affords the title compound as a white solid.

Example 110

3-(4-Fluoro-2-methoxy-phenyl)-1-methyl-1H-pyrazolo[3,4-d]pyrimidin-6-ylamine

This compound is prepared analogously to Example 88 by replacing 2-methoxy-5-trifluoromethylphenylboronic acid with 4-Fluoro-2-methoxyphenylboronic acid to afford the title compound.

Example 111

4-(6-Amino-1-methyl-1H-pyrazolo[3,4-d]pyrimidin-3-yl)-2-trifluoromethyl-phenol

Step 1: 3-(4-Methoxy-3-trifluoromethyl-phenyl)-1-methyl-1H-pyrazolo[3,4-d]pyrimidin-6-ylamine This compound is prepared analogously to Example 88 by replacing 5-trifluoro methyl-2-methoxybenzene boronic acid with 4-methoxy-3-trifluoromethylphenyl boronic acid to afford the title compound.

Step 2: 4-(6-Amino-1-methyl-1H-pyrazolo[3,4-d]pyrimidin-3-yl)-2-trifluoromethyl-phenol 3-(4-Methoxy-3-trifluoromethyl-phenyl)-1-methyl-1H-pyrazolo[3,4-d]pyrimidin-6-ylamine (0.05 g, 0.154 mmol) is suspended in DCM (3 ml) at 0-5° C. (ice-bath), to this mixture is added boron tribromide (1M solution in DCM, 1.24 ml, 1.24 mmol) resulting in a yellow solid. The reaction mixture is stirred at 0-5° C. for 15 minutes then overnight at room temperature, the mixture is quenched with water and stirred for a further 24 hours. The solvents are removed in vacuo and purification by preparative HPLC (water/acetonitrile, 0.1% TFA) affords the title compound as the trifluoroacetate salt.

Example 112

2-(6-Amino-1-methyl-1H-pyrazolo[3,4-d]pyrimidin-3-yl)-6-fluoro-phenol

Step 1: 3-(3-Fluoro-2-methoxy-phenyl)-1-methyl-1H-pyrazolo[3,4-d]pyrimidin-6-ylamine This compound is prepared analogously to Example 88 by replacing 2-methoxy-5-trifluoromethylphenylboronic acid with 3-fluoro-2-methoxyphenylboronic acid to afford the title compound.

Step 2: 2-(6-Amino-1-methyl-1H-pyrazolo[3,4-d]pyrimidin-3-yl)-6-fluoro-phenol

This compound is prepared analogously to Example 111 (step 2) by replacing 3-(4-methoxy-3-trifluoromethyl-phenyl)-1-methyl-1H-pyrazolo[3,4-d]pyrimidin-6-ylamine with 3-(3-Fluoro-2-methoxy-phenyl)-1-methyl-1H-pyrazolo[3,4-d]pyrimidin-6-ylamine to afford the title compound.

Example 113

5-(6-Amino-1-methyl-1H-pyrazolo[3,4-d]pyrimidin-3-yl)-2,4-dimethoxy-benzenesulfonic acid 3-(2,4-Dimethoxy-phenyl)-1-methyl-1H-pyrazolo[3,4-d]pyrimidin-6-ylamine (Example 89) (1 g, 3.50 mmol) is dissolved in concentrated sulfuric acid (25 ml) to give a blood red solution. The reaction mixture is stirred at room temperature overnight, poured onto ice-water (200 ml) and the resulting solid is collected by filtration, washed with water and dried under vacuum to afford the title compound.

Example 114

3-(5-Chloro-2,4-dimethoxy-phenyl)-1-methyl-1H-pyrazolo[3,4-d]pyrimidin-6-ylamine 3-(2,4-Dimethoxy-phenyl)-1-methyl-1H-pyrazolo[3,4-d]pyrimidin-6-ylamine (Example 89) is suspended in acetonitrile (10 ml), trichloroisocyanuric acid (0.021 g, 0.09 mmol) is added and the reaction mixture is stirred for 1.5 hours at room temperature then stood overnight. The solvents are removed in vacuo, the residue is dissolved in EtOAc, washed with water and brine, dried over MgSO$_4$, filtered, concentrated in vacuo and dried under vacuum (45° C.) to afford the title compound.

Example 115

4-(6-Amino-1-methyl-1H-pyrazolo[3,4-d]pyrimidin-3-yl)-2-chloro-6-trifluoromethyl-phenol Step 1: 3-(3-Chloro-4-methoxy-5-trifluoromethyl-phenyl)-1-methyl-1H-pyrazolo[3,4-d]pyrimidin-6-ylamine 3-(4-Methoxy-3-trifluoromethyl-phenyl)-1-methyl-1H-pyrazolo[3,4-d]pyrimidin-6-ylamine (Example 111, step 1) (182 mg, 0.56 mmol) is dissolved in concentrated sulfuric acid (11 ml) to give a red solution. Trichloroisocyanuric acid (44 mg, 0.188 mmol) is added and the reaction mixture is stirred at room temperature overnight then poured onto ice-water. After stirring for 30 minutes, the resulting precipitate is collected by filtration, washed with water and dried under vacuum (45°) to afford the title compound as the sulfate salt.

Step 2: 4-(6-Amino-1-methyl-1H-pyrazolo[3,4-d]pyrimidin-3-yl)-2-chloro-6-trifluoro methyl-phenol This compound is prepared analogously to Example 108 by replacing 3-(3,5-Difluoro-4-methoxy-phenyl)-1-methyl-1H-pyrazolo[3,4-d]pyrimidin-6-ylamine (Example 98) with 3-(3-Chloro-4-methoxy-5-trifluoromethyl-phenyl)-1-methyl-1H-pyrazolo[3,4-d]pyrimidin-6-ylamine sulfate (product from step 1) to afford the title compound.

Example 116

5-(6-Amino-1-methyl-1H-pyrazolo[3,4-d]pyrimidin-3-yl)-2-benzyloxy-3-fluoro-N,N-dimethyl-benzamide This compound is prepared analogously to Example 88 by replacing 2-methoxy-5-trifluoromethylphenylboronic acid with 2-Benzyloxy-3-fluoro-N,N-dimethylbenzamide-5-boronic acid (Intermediate 13) to afford the title compound.

Example 117

4-(6-Amino-1-methyl-1H-pyrazolo[3,4-d]pyrimidin-3-yl)-6-chloro-benzene-1,3-diol This compound is prepared analogously to Example 91 by replacing 3-(2-Methoxy-5-trifluoromethyl-phenyl)-1-methyl-1H-pyrazolo[3,4-d]pyrimidin-6-ylamine (Example 88) with 3-(5-Chloro-2,4-dimethoxy-phenyl)-1-methyl-1H-pyrazolo[3,4-d]pyrimidin-6-ylamine (Example 114). Further purification by preparative HPLC (water/acetonitrile, 0.1% TFA) affords the title compound as the trifluoroacetate salt.

Example 118

3-(3-Chloro-2-methoxy-5-trifluoromethyl-phenyl)-1-methyl-1H-pyrazolo[3,4-d]pyrimidin-6-ylamine 3-(2-Methoxy-5-trifluoromethyl-phenyl)-1-methyl-1H-pyrazolo[3,4-d]pyrimidin-6-ylamine (Example 88) (526 mg, 1.62 mmol) is dissolved in concentrated sulfuric acid (98%, 15 ml) and trichloroisocyanuric acid (126 mg, 0.54 mmol) is added. The reaction mixture is stirred at room temperature for 3 days, poured onto ice water (100 ml) and stirred for 30 minutes. The resulting precipitate is collected by filtration and dried under vacuum to afford the title compound as the sulfate salt.

Example 119

4-(6-Amino-1-methyl-1H-pyrazolo[3,4-d]pyrimidin-3-yl)-2-bromo-6-chloro-benzene-1,3-diol This compound is prepared analogously to Example 97 (step 2) by replacing 2-(6-Amino-1-methyl-4,5-dihydro-1H-pyrazolo[3,4-d]pyrimidin-3-yl)-4-chloro-phenol with 3-(5-Chloro-2,4-dimethoxy-phenyl)-1-methyl-1H-pyrazolo[3,4-d]pyrimidin-6-ylamine (Example 114) to afford the title compound.

Example 120

5-(6-Amino-1-methyl-1H-pyrazolo[3,4-d]pyrimidin-3-yl)-2,4-dimethoxy-N-methyl-benzenesulfonamide

Step 1: 5-(6-Amino-1-methyl-1H-pyrazolo[3,4-d]pyrimidin-3-yl)-2,4-dimethoxy-benzenesulfonyl chloride 5-(6-Amino-1-methyl-1H-pyrazolo[3,4-d]pyrimidin-3-yl)-2,4-dimethoxy-benzenesulfonic acid (Example 113) (629 mg, 1.72 mmol) is suspended in thionyl chloride (25 ml), the reaction mixture is heated to 120° C. for 5 hours then stood overnight at room temperature. The resulting precipitate is removed by filtration, the filtrate is concentrated in vacuo and the resulting residue is azeotroped with toluene to afford the title compound as a solid.

Step 2: 5-(6-Amino-1-methyl-1H-pyrazolo[3,4-d]pyrimidin-3-yl)-2,4-dimethoxy-N-methyl-benzenesulfonamide 5-(6-Amino-1-methyl-1H-pyrazolo[3,4-d]pyrimidin-3-yl)-2,4-dimethoxy-benzenesulfonyl chloride (75 mg, 0.195 mmol) is dissolved in 2M solution $NH_2Me$ in THF (5 ml) and stirred at room temperature for 1 hour. The reaction mixture is concentrated in vacuo and purification by preparative HPLC (water/acetonitrile, 0.1% TFA) affords the title compound as the trifluoroacetate salt.

Example 121

5-(6-Amino-1-methyl-1H-pyrazolo[3,4-d]pyrimidin-3-yl)-N-isopropyl-2,4-dimethoxy-benzenesulfonamide 5-(6-Amino-1-methyl-1H-pyrazolo[3,4-d]pyrimidin-3-yl)-2,4-dimethoxy-benzenesulfonyl chloride (Example 120, Step 1) (82 mg, 0.213 mmol) is suspended in DCM (3 ml), triethylamine (0.323 ml, 0.235 mmol) is added (resulting in a clear solution) followed by iso-propylamine (14 mg, 0.235 mmol). The reaction mixture is stirred for 1 hour at room temperature and then stood overnight. Purification of the crude material by preparative HPLC (water/acetonitrile, 0.1% TFA) affords the title compound as the trifluoroacetate salt.

Example 122

2-(6-Amino-1-methyl-1H-pyrazolo[3,4-d]pyrimidin-3-yl)-6-chloro-4-trifluoromethyl-phenol This compound is prepared analogously to Example 91 by replacing 3-(2-Methoxy-5-trifluoromethyl-phenyl)-1-methyl-1H-pyrazolo[3,4-d]pyrimidin-6-ylamine (Example 88) with 3-(3-Chloro-2-methoxy-5-trifluoromethyl-phenyl)-1-methyl-1H-pyrazolo[3,4-d]pyrimidin-6-ylamine (Example 118) to afford the title compound.

Example 123

3-(2-Methoxy-4-trifluoromethoxy-phenyl)-1-methyl-1H-pyrazolo[3,4-d]pyrimidin-6-ylamine This compound is prepared analogously to Example 88 by replacing 2-methoxy-5-trifluoromethylphenylboronic acid with 2-methoxy-4-(trifluoromethoxy)-phenylboronic acid to afford the title compound.

Example 124

2-(6-Amino-1-methyl-1H-pyrazolo[3,4-d]pyrimidin-3-yl)-5-trifluoromethoxy-phenol A mixture of 3-(2-Methoxy-4-trifluoromethoxy-phenyl)-1-methyl-1H-pyrazolo[3,4-d]pyrimidin-6-ylamine (Example 123) (50 mg, 0.147 mmol) and 1M $BBr_3$ in DCM (3 ml, 2.94 mmol) is stirred at room temperature for 30 minutes. The reaction mixture is quenched with water (5 ml) and stirred for a further 30 minutes. The resulting precipitate is collected by filtration, washed with water and dried under vacuum (50° C.) to afford the title compound as the hydrobromide salt.

Example 125

3-(5-Chloro-2-methoxy-4-trifluoromethoxy-phenyl)-1-methyl-1H-pyrazolo[3,4-d]pyrimidin-6-ylamine This compound is prepared analogously to Example 118 by replacing methoxy-4-trifluoromethyl-phenyl)-1-methyl-1H-pyrazolo[3,4-d]pyrimidin-6-ylamine (Example 88) with 3-(2-Methoxy-4-trifluoromethoxy-phenyl)-1-methyl-1H-pyrazolo[3,4-d]pyrimidin-6-ylamine (Example 123) to afford the title compound as the sulphate salt.

Example 126

6-(6-Amino-1-methyl-1H-pyrazolo[3,4-d]pyrimidin-3-yl)-2-bromo-4-chloro-3-trifluoromethoxy-phenol This compound is prepared analogously to Example 124 by replacing 3-(2-Methoxy-4-trifluoromethoxy-phenyl)-1-methyl-1H-pyrazolo[3,4-d]pyrimidin-6-ylamine (Example 123) with 3-(5-Chloro-2-methoxy-4-trifluoromethoxy-phenyl)-1-methyl-1H-pyrazolo[3,4-d]pyrimidin-6-ylamine (Example 125). Purification by preparative HPLC (water/acetonitrile, 0.1% TFA), affords the title compound as the trifluoroacetate salt.

Example 127

5-(6-Amino-1-methyl-1H-pyrazolo[3,4-d]pyrimidin-3-yl)-N,N-diethyl-2-hydroxy-benzenesulfonamide

Step 1: 5-(6-Amino-1-methyl-1H-pyrazolo[3,4-d]pyrimidin-3-yl)-N,N-diethyl-2-methoxy-benzenesulfonamide This compound is prepared analogously to Example 88 by replacing 2-methoxy-5-trifluoromethylphenylboronic acid with 4-methoxy-3-(N,N-diethylsulfonyl)benzeneboronic acid to afford the title compound.

Step 2: 5-(6-Amino-1-methyl-1H-pyrazolo[3,4-d]pyrimidin-3-yl)-N,N-diethyl-2-hydroxy-benzenesulfonamide This compound is prepared analogously to Example 124 by replacing 3-(2-Methoxy-4-trifluoromethoxy-phenyl)-1-methyl-1H-pyrazolo[3,4-d]pyrimidin-6-ylamine (Example 123) with 5-(6-Amino-1-methyl-1H-pyrazolo[3,4-d]pyrimidin-3-yl)-N,N-diethyl-2-methoxy-benzenesulfonamide and by using 20 eq of $BBr_3$ in DCM to afford the title as the hydrobromide salt.

Example 128

N-[5-(6-Amino-1-methyl-1H-pyrazolo[3,4-d]pyrimidin-3-yl)-2-chloro-phenyl]-methanesulfonamide

Step 1: N-[3-(6-Amino-1-methyl-1H-pyrazolo[3,4-d]pyrimidin-3-yl)-phenyl]-methanesulfonamide This compound is prepared analogously to Example 88 by replacing 2-methoxy-5-trifluoromethylphenylboronic acid with 3-(methylsulfonylamino)phenylboronic acid to afford the title compound.

Step 2: N-[5-(6-Amino-1-methyl-1H-pyrazolo[3,4-d]pyrimidin-3-yl)-2-chloro-phenyl]-methanesulfonamide This compound is prepared analogously to Example 118 by replacing 3-(2-Methoxy-5-trifluoromethyl-phenyl)-1-methyl-1H-pyrazolo[3,4-d]pyrimidin-6-ylamine (Example 88) with N-[3-(6-Amino-1-methyl-1H-pyrazolo[3,4-d]pyrimidin-3-yl)-phenyl]-methanesulfonamide. Purification of the crude residue by preparative HPLC (water/acetonitrile, 0.1% TFA) affords the title compound as the trifluoroacetate salt.

Example 129

5-(6-Amino-1-methyl-1H-pyrazolo[3,4-d]pyrimidin-3-yl)-2-chloro-N-methyl-benzenesulfonamide

Step 1: 3-(4-Chloro-phenyl)-1-methyl-1H-pyrazolo[3,4-d]pyrimidin-6-ylamine

This compound is made analogously to Example 88 by replacing 2-methoxy-5-trifluoromethylphenylboronic acid with 4-(4,4,5,5-tetramethyl-1,3,2-dioxaborolan-2-yl)chlorobenzene. The crude residue is stirred with iso-hexanes: EtOAc, the resulting solid is filtered, washed with iso-hexanes and dried under vacuum to afford the title compound.

Step 2: 5-(6-Amino-1-methyl-1H-pyrazolo[3,4-d]pyrimidin-3-yl)-2-chloro-benzenesulfonyl chloride 3-(4-Chloro-phenyl)-1-methyl-1H-pyrazolo[3,4-d]pyrimidin-6-ylamine (559 mg, 2.15 mmol) is dissolved in chlorosulfonic acid (6.45 ml, 96.84 mmol) and the reaction mixture is heated to 120° C. for 24 hours. After cooling to room temperature the reaction mixture is used crude as a solution for the next step.

Step 3: 5-(6-Amino-1-methyl-1H-pyrazolo[3,4-d]pyrimidin-3-yl)-2-chloro-N-methyl-benzenesulfonamide 2M MeNH$_2$ in THF (30 ml) is cooled to 0-5° C. via an ice-bath, to this is added drop wise 5-(6-Amino-1-methyl-1H-pyrazolo[3,4-d]pyrimidin-3-yl)-2-chloro-benzenesulfonyl chloride (1.625 ml, crude solution from step 2) (exothermic) and the reaction mixture is stirred for 10 minutes at 0-5° C. (ice-bath) resulting in a brown precipitate. The reaction mixture is diluted with water and extracted with EtOAc (2×100 ml). The organic portion is washed with saturated ammonium chloride solution (50 ml), dried over MgSO$_4$, filtered and concentrated in vacuo. Purification of the crude residue by preparative HPLC (water/acetonitrile, 0.1% TFA, affords the title compound as the trifluoroacetate salt.

Example 130

3-(5-Methanesulfonyl-pyridin-3-yl)-1-methyl-1H-pyrazolo[3,4-d]pyrimidin-6-ylamine 3-Bromo-1-methyl-1H-pyrazolo[3,4-d]pyrimidin-6-ylamine (Intermediate 3) (150 mg, 0.66 mmol) and 5-(methylsulfonyl)pyridine-3-boronic acid (200 mg, 0.99 mmol) are suspended in 1,4-dioxane (4 ml). 2M aqueous Na$_2$CO$_3$ (1 ml) is added and the reaction mixture is degassed by bubbling argon through for 5 minutes. Pd(dppf)Cl$_2$ (27 mg, 0.033 mmol) is added and the reaction mixture is heated using microwave radiation at 100° C. for 30 minutes. Water (20 ml) and Et$_2$O (50 ml) are added to the reaction mixture and the resulting grey solid is collected by filtration washing further with water. The solid is suspended in MeOH and excess TFA is added until a solution forms. The organic solvent is reduced in vacuo and the crude residue is purified by reverse phase column chromatography (Isolute™ C18, water/acetonitrile, 0.1% TFA), the appropriate fractions are combined and concentrated in vacuo. The resulting solid is refluxed in EtOH, cooled to room temperature, filtered and dried under vacuum to afford the title compound.

Example 131

3-(1H-Indol-6-yl)-1-methyl-1H-pyrazolo[3,4-d]pyrimidin-6-ylamine

This compound is prepared analogously to Example 130 from the appropriate commercial boronic acid using standard Suzuki coupling methodology. The resulting product after reverse phase column chromatography is further purified by hot trituration in Et$_2$O to afford the title compound.

Example 132

1-Methyl-3-(5-trifluoromethyl-pyridin-3-yl)-1H-pyrazolo[3,4-d]pyrimidin-6-ylamine hydrochloride This compound is prepared analogously to Example 130 by replacing 5-(methylsulfonyl) pyridine-3-boronic acid with 5-trifluoromethylpyridine-3-boronic acid (Intermediate 17). The resulting product after reverse phase column chromatography is suspended in MeOH and 4M HCl in 1,4-dioxane (excess) to form the HCl salt. Further purification by trituration of the solid in MeOH/Et$_2$O affords the title compound.

Example 2-1

N*4*-Benzyl-3-(3-fluoro-4-methoxy-phenyl)-1-methyl-1H-pyrazolo[3,4-d]pyrimidine-4,6-diamine This compound is prepared analogously to Example 88 by replacing 3-Bromo-1-methyl-1H-pyrazolo[3,4-d]pyrimidin-6-ylamine (Intermediate 3) with N*4*-Benzyl-3-bromo-1-methyl-1H-pyrazolo[3,4-d]pyrimidine-4,6-diamine (Intermediate 15) and by replacing 2-methoxy-5-trifluoromethylphenylboronic acid with 3-fluoro-4-methoxyphenylboronic acid to afford the title compound.

Example 2-2

4-[6-Amino-1-methyl-4-(2-morpholin-4-yl-ethylamino)-1H-pyrazolo[3,4-d]pyrimidin-3-yl]-2,6-dichloro-phenol This compound is prepared analogously to Example 88 by replacing 3-Bromo-1-methyl-1H-pyrazolo[3,4-d]pyrimidin- 6-ylamine (Intermediate 3) with 3-Bromo-1-methyl-N*4*-(2-morpholin-4-yl-ethyl)-1H-pyrazolo[3,4-d]pyrimidine-4,6-diamine (Intermediate 16) and by replacing 2-methoxy-5-trifluoromethylphenylboronic acid with 2,6-dichloro-4-(5,5-dimethyl-1,3,2-dioxaborinan-2-yl)phenol to afford the title compound.

Preparation of Intermediates

Intermediate 1

3-Bromo-1-methyl-6-methylsulfanyl-1H-pyrazolo[3,4-d]pyrimidine

Prepared as described in WO 2003029209 (page 45).

Intermediate 2

Trifluoro-methanesulfonic acid 1-methyl-6-methylsulfanyl-1H-pyrazolo[3,4-d]pyrimidin-3-yl ester 1-Methyl-6-methylsulfanyl-1H-pyrazolo[3,4-d]pyrimidin-3-ol (WO 2003029209, page 45) (0.50 g, 2.5 mmol) is dissolved in dry DCM (30 ml) under an inert atmosphere of argon. The reaction mixture is cooled to 0° C. (ice-bath) and pyridine (0.5 ml, 6.0 mmol) is added drop wise followed by triflic anhydride (0.71 g, 0.45 ml, 2.5 mmol) at 0° C. The reaction mixture is stirred for 10 minutes at room temperature. The organic layer is washed with 1.5M HCl (5 ml), saturated $NaHCO_3$ (5 ml), water and brine, dried over $MgSO_4$, filtered and concentrated in vacuo to afford the title compound.

Intermediate 3

3-Bromo-1-methyl-1H-pyrazolo[3,4-d]pyrimidin-6-ylamine

3-Bromo-6-methanesulfonyl-1-methyl-1H-pyrazolo[3,4-d]pyrimidine (WO 2003029209, page 46) (0.215 g, 0.0074 mol) is dissolved in 0.5M ammonia in 1,4-dioxane (11 ml) and stirred overnight at room temperature. The reaction mixture is concentrated in vacuo to afford the title compound.

Intermediate 4

3-Chloro-1-methyl-1H-pyrazolo[3,4-d]pyrimidin-6-ylamine

This is prepared as described in Hauser, Martin; Peters, Earl; Tieckelmann, Howard. Pyrazolono[3,4-d]pyrimidines. II. 6-Methylpyrazolono[3,4-d]pyrimidines and some reactions of pyrazolono[3,4-d]pyrimidines. Journal of Organic Chemistry (1961), 26 451-5.

Intermediate 5

7-Fluoro-5-(4,4,5,5-tetramethyl-[1,3,2]dioxaborolan-2-yl)-1H-indole

Prepared as described in US 2005043347 (page 90)

Intermediate 6

2-Fluoro-4-(4,4,5,5-tetramethyl-[1,3,2]dioxaborolan-2-yl)-phenylamine

A solution containing 4-bromo-2-fluoroaniline (0.50 g, 2.6 mmol), bis(pinacolato)diboron (0.80 g, 3.2 mmol), $Pd(dppf)_2Cl_2$ (0.158 g, 0.21 mmol) and potassium acetate (0.775 g, 7.9 mmol) in dry 1,4-dioxane (20 ml) is degassed for 15 minutes then heated to 85° C. with stirring, under an inert atmosphere of argon, for 18 hours. After cooling to room temperature, the reaction mixture is diluted with EtOAc, filtered through Celite® (filter agent) and washed with water followed by brine. The organic portion is dried over $MgSO_4$, filtered and the solvent removed in vacuo. Purification of the crude residue by flash chromatography on silica, eluting with iso-hexanes:EtOAc (1:1), affords the title compound.

Intermediate 7

3-Bromo-6-methanesulfonyl-1-methyl-1H-pyrazolo[3,4-d]pyrimidine 3-(3,5-Difluoro-phenyl)-1-methyl-1H-pyrazolo[3,4-d]pyrimidin-6-ylamine (Intermediate 1) (9.0 g, 34.7 mmol) is dissolved in dry DCM (250 ml). The reaction mixture is cooled to 0-5° C. (ice-bath) and mCPBA (17.96, 104.1 mmol) is added in small portions over a period of 15 minutes. The reaction mixture is stirred for 1.5 hours at room temperature then diluted with DCM (1000 ml) and washed with saturated $NaHCO_3$ (250 ml) solution followed by brine (250 ml). The organic portion is dried over $MgSO_4$, filtered and concentrated in vacuo to afford the title compound as a white solid.

Intermediate 8

3-Chloro-5-fluoro-4-hydroxyphenyl-boronic acid

4-Bromo-2-chloro-6-fluoro-phenol (0.500 g, 2.21 mmol) is dissolved in dry THF, the reaction mixture is cooled to −78° C. (dry-ice/acetone bath) and 2.5M n-butylithium (1.06 ml, 2.66 mmol) is slowly added drop wise with stirring for 5 minutes. TMSCl (0.298 ml, 2.33 mmol) is added drop wise maintaining the temperature below −70° C. and the reaction mixture is stirred for 30 minutes. Boric acid triethyl ester is then added (0.385 ml, 2.26 mmol) followed by the second addition of n-butylitlium (1.06 ml, 2.66 mmol) maintaining the temperature below −65° C. The reaction mixture is stirred at −70° C. for 30 minutes then quenched with 5M HCl (5 ml) and allowed to warm to room temperature with stirring for 30 minutes. The reaction mixture is diluted with water and EtOAc and the organic portion is washed with 5M NaOH. The aqueous layer is acidified with 5M HCl and extracted with EtOAc, this organic portion is washed with brine, dried over $MgSO_4$ and concentrated in vacuo to afford the title compound as an off white solid.

Intermediate 9

3,5-Difluoro-4-methoxy-phenyl-boronic acid

This compound is prepared analogously to Intermediate 8 by replacing 4-Bromo-2-chloro-6-fluoro-phenol with 5-Bromo-1,3-difluoro-2-methoxy-benzene to afford the title compound.

Intermediate 10

5-(4,4,5,5-Tetramethyl-[1,3,2]dioxaborolan-2-yl)-3-trifluoromethyl-pyridin-2-ylamine Step 1:
5-Bromo-3-trifluoromethyl-pyridin-2-ylamine 2-amino-3-trifluoromethylpyridine (0.980 g, 5.92 mmol) is dissolved in $CHCl_3$ (7 ml) and AcOH (5 ml). The reaction mixture is cooled to 0-10° C. (ice-bath) and bromine (0.424 ml, 8.3 mmol) dissolved in CHCl₃ is slowly added drop wise. The reaction mixture is stirred at this temperature for 1 hour then allowed to warm room temperature. The solvents are removed in vacuo and the residue is dissolved in EtOAc washing with saturated NaHCO₃. The organic portion is dried over MgSO₄, filtered and concentrated to afford the title compound.

Step 2: 5-(4,4,5,5-Tetramethyl-[1,3,2]dioxaborolan-2-yl)-3-trifluoromethyl-pyridin-2-ylamine 5-Bromo-3-trifluoromethyl-pyridin-2-ylamine (1.0 g, 4.14 mmol), bis(pinacolato)diboron (1.26 g, 4.98 mmol), Pd(dppf) Cl₂ (0.90 g, 0.1242 mmol), potassium acetate (1.14 g, 11.6 mmol) and dry DMF (20 ml) are mixed together under an inert atmosphere of argon and heated using microwave radiation at 150° C. for 2 hours. The reaction mixture is cooled to room temperature, filtered through Celite® (filter agent) and concentrated in vacuo. The resulting residue is dissolved in EtOAc and loaded onto an Isolute™ SCX column (silica based cation exchange sorbent) eluting with 200 ml 0.35M NH₃ in methanol. The methanolic ammonia fractions are combined, concentrated in vacuo and dried under vacuum to afford the title compound. [M+H]⁺ 381

Intermediate 11

2,6-Difluoro-4-(4,4,5,5-tetramethyl-[1,3,2]dioxaborolan-2-yl)-benzonitrile

4-Bromo-2,6-difluoro-benzonitrile (0.278 g, 1.03 mmol), bis(pinacolato)diboron (0.278 g, 1.03 mmol), Pd(dppf)₂Cl₂ (0.02 g, 0.0275 mmol), potassium acetate (251 g, 2.568 mmol) and dry DMF (4 ml) are mixed together and heated using microwave radiation at 130° C. for 30 minutes. The reaction mixture is cooled to room temperature, filtered through Celite® (filter agent) washing with EtOAc and the filtrate is concentrated in vacuo to afford the title compound.

Intermediate 12

N-[3-Fluoro-2-methoxy-5-(4,4,5,5-tetramethyl-[1,3,2]dioxaborolan-2-yl)-phenyl]-acetamide This compound is prepared analogously to Intermediate 6 by replacing 4-bromo-2-fluoroaniline with N-(5-Bromo-3-fluoro-2-methoxy-phenyl)-acetamide to afford the title compound [M+H]⁺ 310.

Intermediate 13

2-Benzyloxy-3-fluoro-N,N-dimethylbenzamide-5-boronic acid

Step 1:
2-Benzyloxy-5-bromo-3-fluoro-benzaldehyde

To a solution of 5-Bromo-3-fluoro-2-hydroxy-benzaldehyde (5 g, 22.8 mmol) in DMF (100 ml) is added benzyl bromide (5.7 ml, 48 mmol) and cesium carbonate (11.9 g, 37 mmol). The reaction mixture is stirred at room temperature for 20 hours then diluted with water (150 ml) and extracted with EtOAc (2×150 ml), the organic portions are combined, washed with brine (50 ml), dried over MgSO₄ and concentrated in vacuo to give a waxy off-white solid. The solid is stirred in iso-hexanes (30 ml) for 30 minutes, filtered and dried under vacuum to afford the title compound.

Step 2: 2-Benzyloxy-5-bromo-3-fluoro-benzoic acid

This compound is prepared as described in Micklatcher, Mark L.; Cushman, Mark: An Improved Method for the Synthesis of 3-Fluorosalicylic Acid with Application to the Synthesis of 3-(Trifluoromethyl)salicylic Acid. Synthesis (1999), 11, 1878-1880.

Step 3: 2-Benzyloxy-5-bromo-3-fluoro-N,N-dimethyl-benzamide

2-Benzyloxy-5-bromo-3-fluoro-benzoic acid (product from step 2) (0.2 g, 0.615 mmol) is dissolved in THF (10 ml) and treated with 2M dimethylamine in THF (0.308 ml), N-methylmorpholine (0.270 ml, 2.46 mmol) and HATU (0.234 g, 0.615 mmol) and stirred at room temperature overnight. The reaction mixture is diluted with 2M HCl and extracted with EtOAc (2×), the organic portions are combined washed with brine, dried over MgSO₄ and concentrated in vacuo. The resulting crude residue is dry loaded onto silica and purification by flash chromatography eluting with EtOAc affords the title compound as a white solid.

Step 4: 2-Benzyloxy-3-fluoro-N,N-dimethylbenzamide-5-boronic acid

This compound is prepared analogously to Intermediate 8 by replacing 4-Bromo-2-chloro-6-fluoro-phenol with 2-Benzyloxy-5-bromo-3-fluoro-N,N-dimethyl-benzamide (product from step 3) to afford the title compound.

Intermediate 14

3-Bromo-4-chloro-1-methyl-1H-pyrazolo[3,4-d]pyrimidin-6-ylamine

Step 1:
4-Chloro-1H-pyrazolo[3,4-d]pyrimidin-6-ylamine

2-Amino-4,6-dichloro-pyrimidine-5-carbaldehyde (5 g, 26.04 mmol) is dissolved in THF (125 ml), Et₃N (4.13 ml, 29.6 mmol) is added followed by hydrazine monohydrate (1.19 g, 26.04 mmol) in water (15 ml) and the reaction mixture is stirred at room temperature for 1.5 hours. The organic solvent is removed in vacuo and a further 30 ml of water is added to the reaction mixture. The resulting precipitate is collected by filtration and dried under vacuum to afford the title compound.

Step 2: 3-Bromo-4-chloro-1H-pyrazolo[3,4-d]pyrimidin-6-ylamine

N-bromosuccinimide (673 mg, 3.8 mmol) is added to a suspension of 4-Chloro-1H-pyrazolo[3,4-d]pyrimidin-6-ylamine (500 mg, 2.96 mmol) in dichloroethane (30 ml) and heated to reflux overnight. The reaction mixture is cooled to room temperature and the solvent is removed in vacuo. The resulting solid is diluted with water, stirred for 30 minutes at room temperature, then collected by filtration to afford the title compound.

Step 3: 3-Bromo-4-chloro-1-methyl-1H-pyrazolo[3,4-d]pyrimidin-6-ylamine

3-Bromo-4-chloro-1H-pyrazolo[3,4-d]pyrimidin-6-ylamine (580 mg, 2.3 mmol) is dissolved in DMF (40 ml), potassium hydroxide (131 mg, 2.3 mmol) is added and the reaction mixture is stirred at room temperature for 15 minutes. Methyl iodide (0.133 ml, 2.3 mmol) is then added and the reaction is continued stirring overnight. The reaction mixture is diluted with water (60 ml) and EtOAc (60 ml), the layers are separated and the organic portion is washed with brine, dried over MgSO$_4$, filtered and concentrated in vacuo to afford the title compound.

Intermediate 15

N*4*-Benzyl-3-bromo-1-methyl-1H-pyrazolo[3,4-d]pyrimidine-4,6-diamine

3-Bromo-4-chloro-1-methyl-1H-pyrazolo[3,4-d]pyrimidin-6-ylamine (Intermediate 14) (160 mg, 0.61 mmol), benzylamine (0.2 ml, 1.83 mmol) and DMF (5 ml) are mixed together and heated at 40° C. overnight. After cooling to room temperature the solvent is removed in vacuo and the residue is dissolved in methanol (30 ml) and passed through an Isolute™ CBA column (silica based carboxylic acid sorbent). Silica gel is added to the filtrate, the solvent is removed in vacuo and the resulting residue is flash chromatographed eluting with EtOAc:iso-hexanes (4:6) and then increasing to EtOAc:iso-hexanes (1:1). The appropriate fractions are collected and concentrated in vacuo to afford the title compound.

Intermediate 16

3-Bromo-1-methyl-N*4*-(2-morpholin-4-yl-ethyl)-1H-pyrazolo[3,4-d]pyrimidine-4,6-diamine 3-Bromo-4-chloro-1-methyl-1H-pyrazolo[3,4-d]pyrimidin-6-ylamine (Intermediate 14) (750 mg, 2.8 mmol), 2-(4-morpholinyl)ethylamine (0.44 ml, 3.3 mmol) and DMF (30 ml) are mixed together and heated to 50° C. overnight. After cooling to room temperature the reaction mixture is diluted with DCM (60 ml) and water (40 ml) and the aqueous portion is extracted with a further 40 ml DCM. The organic portions are combined, dried over MgSO4, filtered and concentrated in vacuo. The crude residue is dry loaded onto silica and purification by flash chromatography eluting with DCM then MeOH:DCM (5:95) affords the title compound.

Intermediate 17

5-Trifluoromethylpyridine-3-boronic acid

A cooled (−78° C.) solution of 3-bromo-5-(trifluoromethyl)pyridine (5 g, 22.1 mmol) in dry THF (50 ml), under an inert atmosphere of argon, is treated with triethyl borate (3.39 g, 23.21 mmol) followed by drop wise addition of 1.46M n-BuLi in hexanes (15.2 ml, 24.34 mmol). The reaction mixture is allowed to warm to room temperature overnight and treated with 5M HCl (100 ml). After stirring for 30 minutes, the THF is removed in vacuo and the aqueous layer is extracted with EtOAc (4×100 ml). The aqueous portion is concentrated in vacuo and dried under vacuum overnight to afford the title compound as the hydrochloride salt. [M+H]$^+$ 168.

The invention claimed is:
1. A compound of formula (I)

(I)

or a pharmaceutically acceptable salt thereof, wherein:
$R^1$ is unsubstituted $C_1$-$C_3$-alkyl;
$R^2$ is phenyl having the substitution pattern, where the $R^2$ phenyl is fused at $R^4$-$R^5$, $R^5$-$R^6$, $R^6$-$R^7$ or $R^7$-$R^8$ by a heteroaryl group selected from thienyl, furanyl, pyrrolyl, pyrazolyl, imidazolyl, oxazolyl, isoxazolyl, thiazolyl, and isothiazolyl, a $C_4$-$C_6$ carbocyclic group or a 6 membered heterocyclyl group, where the fused heteroaryl group is independently optionally substituted by one or more groups selected from List X;
List X represents hydroxyl, cyano, nitro, $C_1$-$C_8$-alkyl, $C_1$-$C_8$-alkoxy, halogen, formyl, amino, $C_1$-$C_8$-alkylamino, di-$C_1$-$C_8$-alkylamino, $C_1$-$C_8$-alkylamidino, —N(H)C(=NH)$C_1$-$C_8$-alkyl, —N($C_1$-$C_8$-alkyl)C(=NH)$C_1$-$C_8$-alkyl, $C_1$-$C_8$-alkylaminocarbonyl, di-$C_1$-$C_8$-alkylaminocarbonyl, aminocarbonylamino, aminocarbonyl($C_1$-$C_8$-alkyl)amino, $C_1$-$C_8$-alkylaminocarbonylamino, di-$C_1$-$C_8$-alkylaminocarbonylamino, $C_1$-$C_8$-alkylaminocarbonyl($C_1$-$C_8$-alkyl)amino, di-$C_1$-$C_8$-alkylaminocarbonyl($C_1$-$C_8$-alkyl)amino, $C_1$-$C_8$-alkylcarbonylamino, $C_1$-$C_8$-alkylcarbonyl($C_1$-$C_8$-alkyl)amino, $C_1$-$C_8$-alkylthiocarbonylamino, $C_1$-$C_8$-alkylthiocarbonyl($C_1$-$C_8$-alkyl)amino, hydroxysulfonyl, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl;
$R^3$ is hydrogen, amino or $C_1$-$C_3$-alkylamino;
Y represents hydrogen, $C_1$-$C_8$-alkyl, $C_1$-$C_8$-alkoxy where each of the afore-mentioned hydrocarbon groups may be optionally substituted, where chemically feasible, by one or more halogen, hydroxyl, amino, $C_1$-$C_8$-alkylamino, di-$C_1$-$C_8$-alkylamino or $C_1$-$C_8$-alkoxy groups, or Y represents the group —($C_0$-$C_4$-alkylene)-N($R^{15}$)$R^{16}$; and
$R^{15}$ and $R^{16}$ independently represent hydrogen or $C_1$-$C_4$-alkyl, or $R^{15}$ is hydrogen and $R^{16}$ is $C_1$-$C_4$-alkyl substituted by phenyl, a 5-6 membered heteroaryl group, a $C_4$-$C_6$ carbocyclic group or a 5-6 membered heterocyclyl group, where said rings are optionally substituted by one or more hydroxyl, nitro, $C_1$-$C_8$-alkyl, $C_1$-$C_8$-alkoxy, halogen, amino, $C_1$-$C_8$-alkylamino, di-$C_1$-$C_8$-alkylamino, $C_1$-$C_8$-alkylsulfonyl, aminosulfonyl, $C_1$-$C_8$-alkylaminosulfonyl or di-$C_1$-$C_8$-alkylaminosulfonyl groups, where each of the afore-mentioned hydrocarbon groups may be optionally substituted, where chemically feasible by one or more halogen, hydroxyl, amino, $C_1$-$C_4$-alkylamino, di-$C_1$-$C_4$-alkylamino or $C_1$-$C_4$-alkoxy groups, or $R^{15}$ and $R^{16}$ together with the N to which they are attached form a 5-6-membered heterocyclic ring.

2. The compound of formula (I) according to claim 1, or a pharmaceutically acceptable salt thereof, wherein $R^1$ is methyl.

3. The compound or a pharmaceutically acceptable salt thereof according to claim 1, wherein
$R^2$ is phenyl having the substitution pattern,

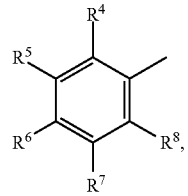

where the $R^2$ phenyl is fused at $R^5$-$R^6$ by a heteroaryl group selected from thienyl, furanyl, pyrrolyl, pyrazolyl, imidazolyl, oxazolyl, isoxazolyl, thiazolyl, and isothiazolyl, where the fused heteroaryl group is independently optionally substituted by one or more groups selected from List X.

4. The compound or pharmaceutically acceptable salt thereof according to claim 1, wherein
List X represents hydroxyl, cyano, nitro, $C_1$-$C_8$-alkyl, $C_1$-$C_8$-alkoxy, halogen, formyl, amino, $C_1$-$C_8$-alkylamino, di-$C_1$-$C_8$-alkylamino, $C_1$-$C_8$-alkylsulfonyl, aminosulfonyl, $C_1$-$C_8$-alkylaminosulfonyl or di-$C_1$-$C_8$-alkylaminosulfonyl.

5. The compound or pharmaceutically acceptable salt thereof according to claim 1, wherein $R^3$ is amino.

6. The compound or pharmaceutically acceptable salt thereof according to claim 1, wherein Y is hydrogen or —($C_0$-$C_4$-alkylene)-N($R^{15}$)$R^{16}$; and
$R^{15}$ and $R^{16}$ independently represent hydrogen or $C_1$-$C_4$-alkyl.

7. A pharmaceutical composition, comprising:
the compound according to claim 1 or a pharmaceutically acceptable salt thereof, and
a suitable carrier or excipient.

8. A compound of formula (I)

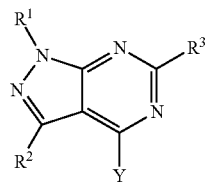

(I)

or a pharmaceutically acceptable salt thereof, wherein:
$R^1$ is unsubstituted $C_1$-$C_3$-alkyl;
$R^2$ is phenyl having the substitution pattern,

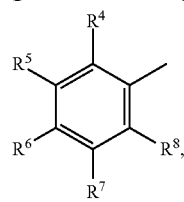

wherein the $R^2$ phenyl is fused at $R^4$-$R^5$, $R^5$-$R^6$, $R^6$-$R^7$ or $R^7$-$R^8$ by a heteroaryl group selected from pyrazolyl, imidazolyl, oxazolyl, isoxazolyl, thiazolyl, and isothiazolyl, a $C_4$-$C_6$ carbocyclic group or a 6 membered heterocyclyl group, where the fused heteroaryl group is independently optionally substituted by one or more groups selected from List X;
List X represents hydroxyl, cyano, nitro, $C_1$-$C_8$-alkyl, $C_2$-$C_8$-alkenyl, $C_2$-$C_8$-alkynyl, $C_1$-$C_8$-alkoxy, $C_1$-$C_8$-alkenyloxy, $C_1$-$C_8$-alkynyloxy, phenyl, a 5-6 membered heteroaryl group, a $C_4$-$C_6$ carbocyclic group or a 5-6 membered heterocyclyl group, —($C_0$-$C_4$-alkylene)-O—($C_1$-$C_4$-alkylene)-$R^9$, ($C_0$-$C_4$-alkylene)-O—($C_2$-$C_4$-alkylene)-$R^{10}$, ($C_0$-$C_4$-alkylene)-N($R^{11}$)—($C_1$-$C_4$-alkylene)-$R^{12}$, —($C_0$-$C_4$-alkylene)-N($R^{13}$)—($C_2$-$C_4$-alkylene)-$R^{14}$, halogen, formyl, $C_1$-$C_8$-alkylcarbonyl, carboxy, $C_1$-$C_8$-alkoxycarbonyl, $C_1$-$C_8$-alkylaminooxycarbonyl, di-$C_1$-$C_8$-alkylaminooxycarbonyl, amino, $C_1$-$C_8$-alkylamino, di-$C_1$-$C_8$-alkylamino, $C_1$-$C_8$-alkylamidino, —N(H)C(=NH)$C_1$-$C_8$-alkyl, —N($C_1$-$C_8$-alkyl)C(=NH)$C_1$-$C_8$-alkyl, $C_1$-$C_8$-alkylaminocarbonyl, di-$C_1$-$C_8$-alkylaminocarbonyl, aminocarbonylamino, aminocarbonyl($C_1$-$C_8$-alkyl)amino, $C_1$-$C_8$-alkylaminocarbonylamino, di-$C_1$-$C_8$-alkylaminocarbonylamino, $C_1$-$C_8$-alkylaminocarbonyl($C_1$-$C_8$-alkyl)amino, di-$C_1$-$C_8$-alkylaminocarbonyl($C_1$-$C_8$-alkyl)amino, $C_1$-$C_8$-alkylcarbonylamino, $C_1$-$C_8$-alkylcarbonyl($C_1$-$C_8$-alkyl)amino, $C_1$-$C_8$-alkylthiocarbonylamino, $C_1$-$C_8$-alkylthiocarbonyl($C_1$-$C_8$-alkyl)amino, hydroxysulfonyl, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl, where each of the afore-mentioned hydrocarbon groups may be optionally substituted, where chemically feasible, by one or more halogen, hydroxyl, amino, $C_1$-$C_4$-alkylamino, di-$C_1$-$C_4$-alkylamino or $C_1$-$C_4$-alkoxy groups and where said cyclic groups may be optionally substituted by one or more hydroxyl, cyano, nitro, $C_1$-$C_8$-alkyl, $C_1$-$C_8$-alkenyl, $C_1$-$C_8$-alkenyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups;
$R^9$ and $R^{12}$ independently represent hydrogen, $C_1$-$C_4$-alkenyl, $C_1$-$C_4$-alkynyl, halogen, cyano, nitro, $C_1$-$C_8$-alkylcarbonyl, carboxy, $C_1$-$C_8$-alkoxycarbonyl, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl, di-$C_1$-$C_8$-alkylaminosulfonyl, phenyl, a C-linked 5-6 membered heteroaryl group, a $C_4$-$C_6$ carbocyclic group or a C-linked 5-6 membered heterocyclyl group, where said phenyl or cyclic groups may be optionally substituted by one or more hydroxyl, cyano, nitro, $C_1$-$C_8$-alkyl, $C_1$-$C_8$-alkenyl, $C_1$-$C_8$-alkenyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups;

$R^{10}$ and $R^{14}$ independently represent hydroxyl, $C_1$-$C_4$-alkoxy, $C_1$-$C_4$-alkenyloxy, $C_1$-$C_4$-alkynyloxy, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, an N-linked 5-6 membered heteroaryl group or an N-linked 5-6 membered heterocyclyl, where said cyclic groups may be optionally substituted by one or more hydroxyl, nitro, $C_1$-$C_8$-alkyl, $C_1$-$C_8$-alkenyl, $C_1$-$C_8$-alkynyl, $C_1$-$C_8$-alkoxy, $C_1$-$C_8$-alkenyloxy, $C_1$-$C_8$-alkynyloxy, halogen, $C_1$-$C_8$-alkylcarbonyl, carboxy, $C_1$-$C_8$-alkoxycarbonyl, amino, $C_1$-$C_8$-alkylamino, di-$C_1$-$C_8$-alkylamino, $C_1$-$C_8$-alkylaminocarbonyl, di-$C_1$-$C_8$-alkylaminocarbonyl, $C_1$-$C_8$-alkylcarbonylamino, $C_1$-$C_8$-alkylcarbonyl($C_1$-$C_8$-alkyl)amino, $C_1$-$C_8$-alkylsulfonylamino, $C_1$-$C_8$-thioalkyl, $C_1$-$C_8$-alkylsulfinyl, $C_1$-$C_8$-alkylsulfonyl, aminosulfonyl, $C_1$-$C_8$-alkylaminosulfonyl or di-$C_1$-$C_8$-alkylaminosulfonyl groups;

$R^{11}$ and $R^{13}$ independently represent hydrogen or $C_1$-$C_6$-alkyl;

$R^3$ is hydrogen;

Y represents the group —$N(R^{15})R^{16}$; and $R^{15}$ and $R^{16}$ independently represent hydrogen or $C_1$-$C_4$-alkyl.

9. The compound according to claim 8, or a pharmaceutically acceptable salt thereof, wherein $R^1$ is $C_1$-$C_3$-alkyl;

$R^2$ is phenyl having the substitution pattern,

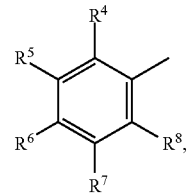

wherein the $R^2$ phenyl is fused at $R^4$-$R^5$, $R^5$-$R^6$, $R^6$-$R^7$ or $R^7$-$R^8$ by a heteroaryl group selected from pyrazolyl, imidazolyl, oxazolyl, and isoxazolyl, where the fused heteroaryl group is independently optionally substituted by one or more groups selected from List X;

List X represents hydroxyl, cyano, nitro, amino, $C_1$-$C_8$-alkylamino, di-$C_1$-$C_8$-alkylamino, or $C_1$-$C_8$-alkylamidino;

$R^3$ is hydrogen;

Y is —$NH_2$.

10. The compound of claim 3, or a pharmaceutically acceptable salt thereof, wherein $R^3$ is hydrogen, amino or methylamino.

11. The compound or pharmaceutically acceptable salt thereof according to claim 10, wherein List X represents hydroxyl, cyano, nitro, $C_1$-$C_8$-alkyl, $C_1$-$C_8$-alkoxy, halogen, formyl, amino, $C_1$-$C_8$-alkylamino, di-$C_1$-$C_8$-alkylamino, $C_1$-$C_8$-alkylsulfonyl, aminosulfonyl, $C_1$-$C_8$-alkylaminosulfonyl or di-$C_1$-$C_8$-alkylaminosulfonyl.

12. The compound or pharmaceutically acceptable salt of claim 4, wherein $R^3$ is hydrogen, amino or methylamino.

13. A pharmaceutical composition, comprising the compound according to claim 9 or a pharmaceutically acceptable salt thereof, and a suitable carrier or excipient.

* * * * *